US011832988B2

(12) United States Patent
Fukuyo

(10) Patent No.: US 11,832,988 B2
(45) Date of Patent: Dec. 5, 2023

(54) MAMMOGRAPHY APPARATUS, METHOD FOR OPERATING MAMMOGRAPHY APPARATUS, IMAGE PROCESSING APPARATUS, PROGRAM FOR OPERATING IMAGE PROCESSING APPARATUS, AND METHOD FOR OPERATING IMAGE PROCESSING APPARATUS

(71) Applicant: FUJIFILM Corporation, Tokyo (JP)

(72) Inventor: Masakazu Fukuyo, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 1061 days.

(21) Appl. No.: 16/565,492

(22) Filed: Sep. 10, 2019

(65) Prior Publication Data

US 2020/0100760 A1 Apr. 2, 2020

(30) Foreign Application Priority Data

Sep. 27, 2018 (JP) .................................. 2018-182764

(51) Int. Cl.
*A61B 8/08* (2006.01)
*A61B 8/00* (2006.01)
(Continued)

(52) U.S. Cl.
CPC .......... *A61B 8/0825* (2013.01); *A61B 6/0414* (2013.01); *A61B 8/403* (2013.01);
(Continued)

(58) Field of Classification Search
CPC ..... A61B 8/0825; A61B 6/0414; A61B 8/403; A61B 8/4416; A61B 8/52; A61B 6/4417; A61B 6/502
See application file for complete search history.

(56) References Cited

U.S. PATENT DOCUMENTS 7,756,246 B2 * 7/2010 Mikami ............... A61B 6/0414
378/37
8,831,708 B2 * 9/2014 Paladini ............... A61B 8/4483
601/2
(Continued)

FOREIGN PATENT DOCUMENTS

JP 2008173291 7/2008
JP 2009219656 10/2009
(Continued)

OTHER PUBLICATIONS

"Search Report of Europe Counterpart Application", dated Feb. 4, 2020, p. 1-p. 9.

(Continued)

*Primary Examiner* — Baisakhi Roy
(74) *Attorney, Agent, or Firm* — JCIPRNET

(57) ABSTRACT

A mammography apparatus performs ultrasound imaging while moving an ultrasound transceiver having an ultrasound imaging region smaller than a radiography region from a scanning start position to a scanning end position for scanning. During the scanning, in plural states in which the ultrasound transceiver is disposed at different positions of the radiography region, the radiation source emits radiation to perform radiography. A control device acquires plural captured radiographic images. Then, a removed radiographic image, in which an image of the ultrasound transceiver disposed at different positions in the plural radiographic images has been removed, is generated.

17 Claims, 17 Drawing Sheets

(51) Int. Cl.
*A61B 6/04* (2006.01)
*A61B 6/00* (2006.01)

(52) U.S. Cl.
CPC .............. *A61B 8/4416* (2013.01); *A61B 8/52* (2013.01); *A61B 6/4417* (2013.01); *A61B 6/502* (2013.01)

(56) References Cited

U.S. PATENT DOCUMENTS

| | | | | |
|---|---|---|---|---|
| 2002/0193849 | A1* | 12/2002 | Fenn | A61N 5/02 607/101 |
| 2003/0004454 | A1* | 1/2003 | Fenn | A61N 5/02 604/20 |
| 2003/0055471 | A1* | 3/2003 | Fenn | A61N 5/02 607/101 |
| 2009/0016580 | A1* | 1/2009 | Yamamichi | A61B 6/502 382/128 |
| 2009/0234229 | A1 | 9/2009 | Mikami et al. | |
| 2009/0290679 | A1 | 11/2009 | Mikami et al. | |
| 2010/0014738 | A1* | 1/2010 | Birnholz | G06T 7/0012 382/128 |
| 2010/0166147 | A1 | 7/2010 | Abenaim | |
| 2013/0237814 | A1 | 9/2013 | Marcovici | |
| 2014/0180082 | A1 | 6/2014 | Evans et al. | |
| 2017/0360389 | A1 | 12/2017 | Ochiai et al. | |
| 2018/0055479 | A1* | 3/2018 | Lalena | A61B 8/4461 |
| 2019/0307334 | A1* | 10/2019 | Wang | A61B 5/0095 |
| 2020/0100760 | A1* | 4/2020 | Fukuyo | A61B 6/0414 |
| 2020/0138518 | A1* | 5/2020 | Lang | A61B 5/05 |

FOREIGN PATENT DOCUMENTS

| | | |
|---|---|---|
| JP | 2009-279111 | 12/2009 |
| JP | 2013000583 | 1/2013 |

OTHER PUBLICATIONS

Office Action of Japan Counterpart Application, with English translation thereof, dated Aug. 10, 2021, pp. 1-8.

\* cited by examiner

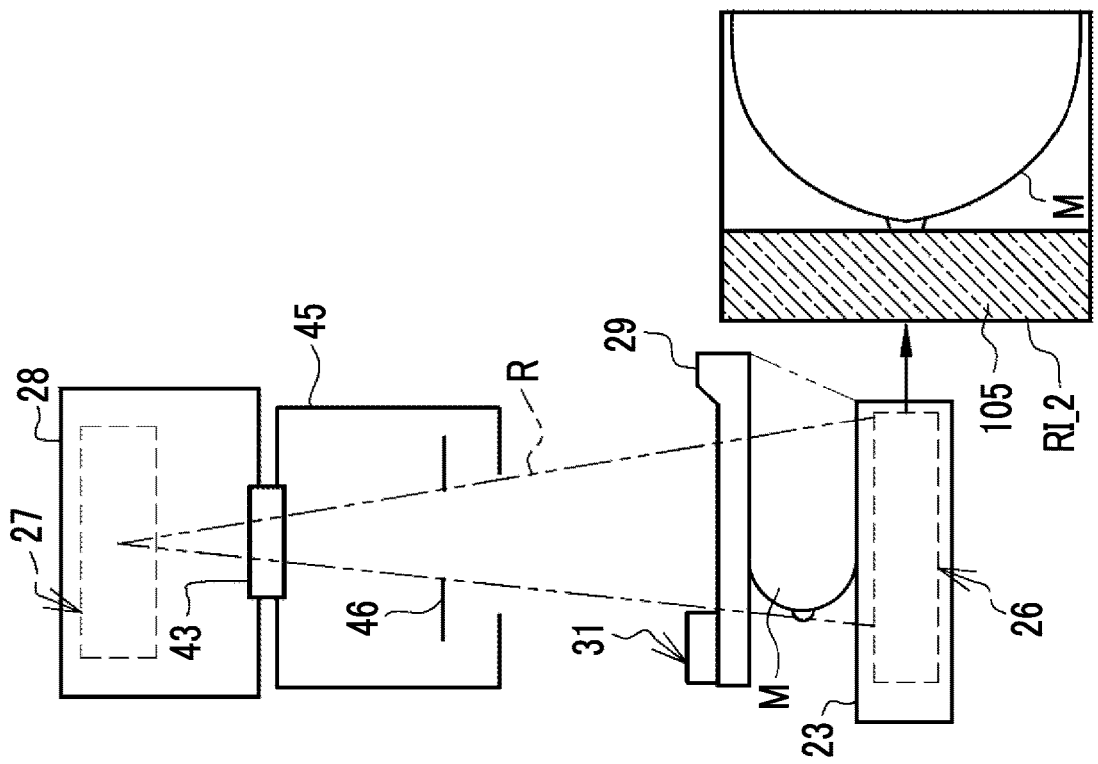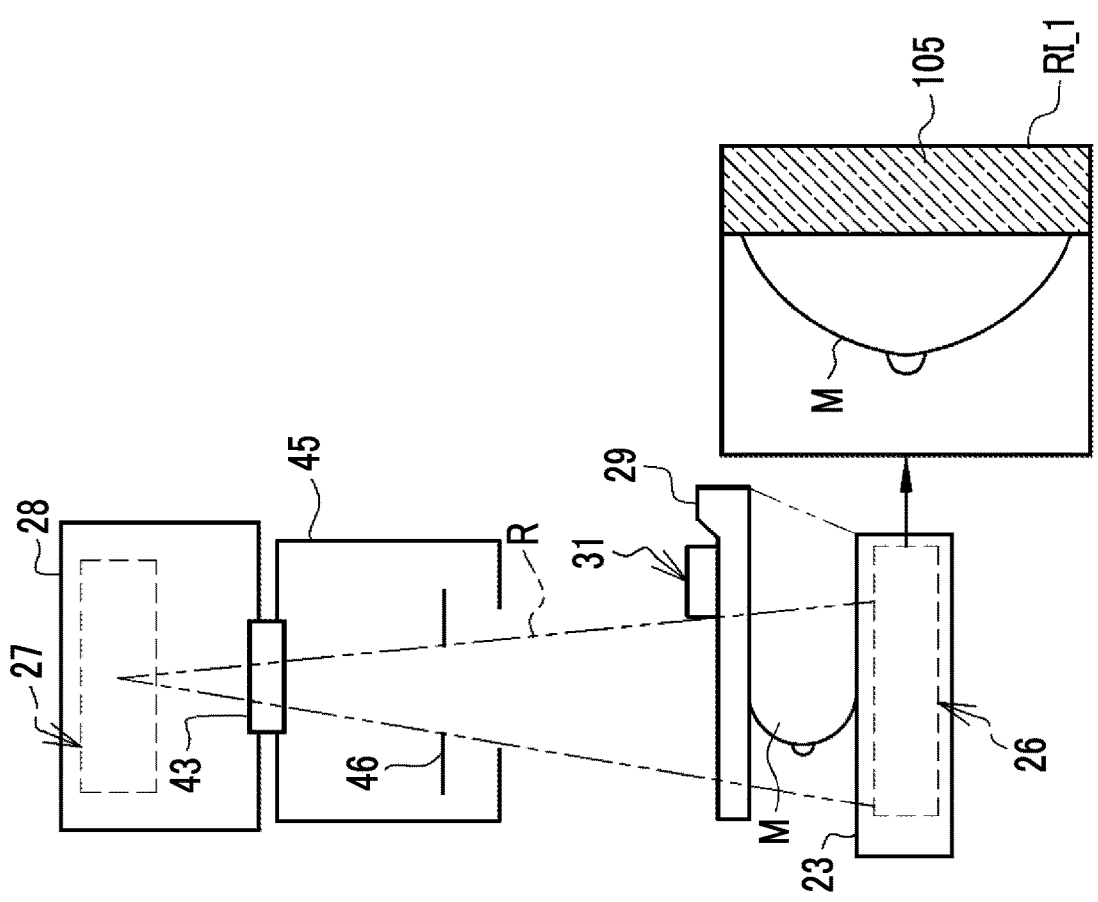

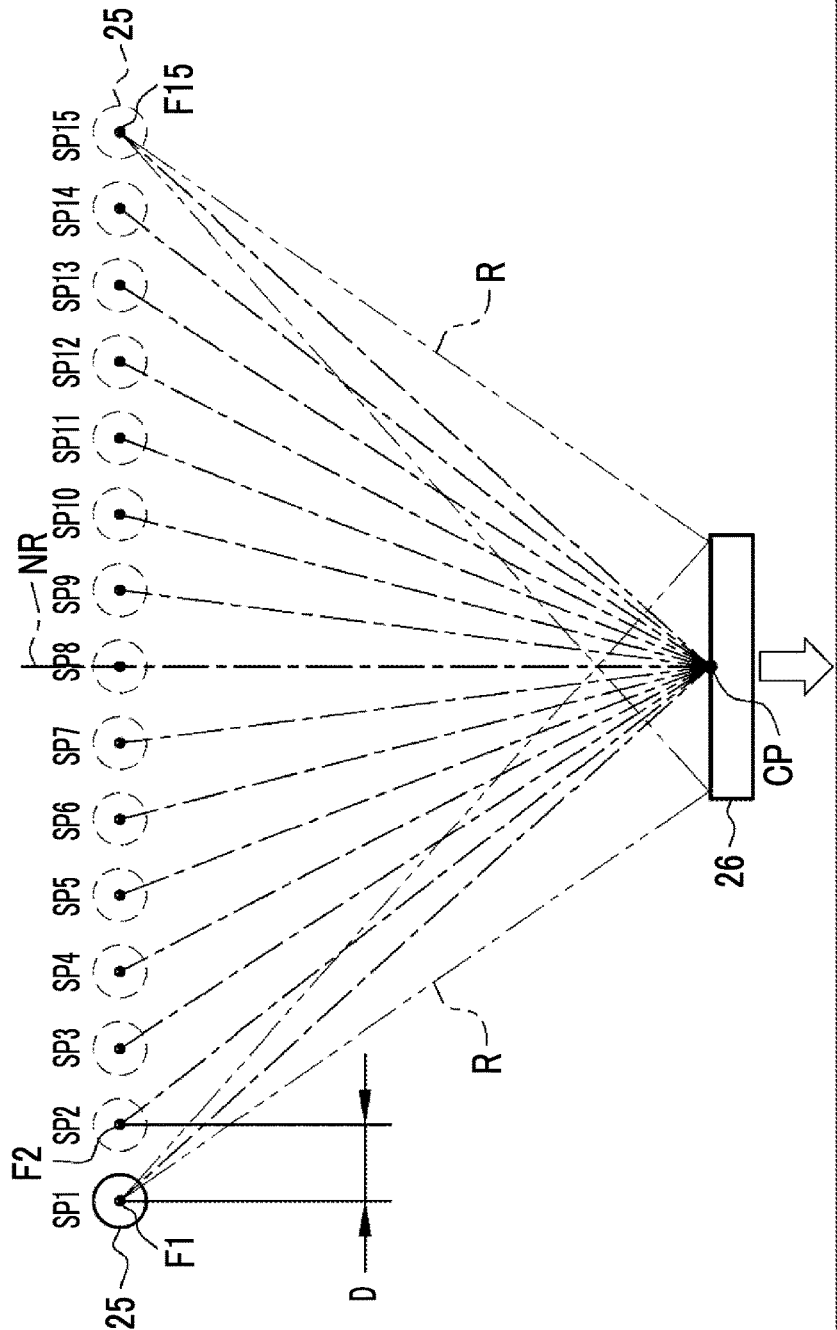

MAMMOGRAPHY APPARATUS, METHOD FOR OPERATING MAMMOGRAPHY APPARATUS, IMAGE PROCESSING APPARATUS, PROGRAM FOR OPERATING IMAGE PROCESSING APPARATUS, AND METHOD FOR OPERATING IMAGE PROCESSING APPARATUS

CROSS-REFERENCE TO RELATED APPLICATION

This application claims priority from Japanese Patent Application No. 2018-182764, filed Sep. 27, 2018, the disclosure of which is incorporated herein by reference in its entirety.

BACKGROUND

Technical Field

The technology according to the present disclosure relates to a mammography apparatus, a method for operating the mammography apparatus, an image processing apparatus, a program for operating the image processing apparatus, and a method for operating the image processing apparatus.

Related Art

A mammography apparatus has been known which captures a radiographic image of the breast. A technique has been proposed which captures an ultrasound image of the breast in addition to the radiographic image in order to increase the accuracy of detecting breast cancer in the mammography apparatus. For example, JP2009-279111A discloses a mammography apparatus comprising a radiation source that irradiates the breast with radiation, a radiation detector in which pixels detecting the radiation transmitted through the breast are two-dimensionally arranged, and an ultrasound transceiver including ultrasound transducers that transmit ultrasonic waves to the breast and receive ultrasound echoes from the breast.

In JP2009-279111A, the ultrasound transceiver has an ultrasound transducer array in which the ultrasound transducers are two-dimensionally arranged. The ultrasound transceiver is made of a material that transmits radiation and is provided between the radiation source and the radiation detector. In order to facilitate the comparison between a radiographic image and an ultrasound image, a region (hereinafter, referred to as a radiography region) in which the pixels of the radiation detector are arranged and a region (hereinafter, referred to as an ultrasound imaging region) in which the ultrasound transducers of the ultrasound transceiver are arranged have substantially the same size and have substantially the same positional relationship with the breast. Therefore, in JP2009-279111A, the ultrasound transceiver is fixed without being moved.

From the positional relationship that the ultrasound transceiver is provided between the radiation source and the radiation detector, the image of the ultrasound transceiver is included in the radiographic image. Therefore, in JP2009-279111A, image processing for removing the image of the ultrasound transceiver from the radiographic image is performed. Specifically, a radiographic image is captured in advance in a state in which the breast is not set. Then, the radiographic image captured in the state in which the breast is not set is subtracted from the actual radiographic image captured in a state in which the breast is set. Alternatively, Fourier transform is performed for the actual radiographic image, spatial frequency components caused by the array pitch of the ultrasound transducers are removed, and inverse Fourier transform is performed.

In the mammography apparatus disclosed in JP2009-279111A, the ultrasound transceiver needs to be made of a material that transmits radiation. As a result, the ultrasound transceiver is very special. In addition, even though the ultrasound transceiver is made of a material that transmits radiation, the radiation reaching a radiography region of the radiation detector is attenuated since the ultrasound transceiver covers almost the entire radiography region. Therefore, it is necessary to increase the dose of radiation emitted from the radiation source, as compared to a case in which the ultrasound transceiver is not provided, in order to make a desired dose of radiation reach the radiography region. In addition, even though image processing for removing the image of the ultrasound transceiver from the radiographic image is performed, the image of the ultrasound transceiver becomes noise in the radiographic image. Therefore, it is preferable that the image of the ultrasound transceiver is not included in the radiographic image from the beginning.

For this reason, the inventors examined a method for capturing a radiographic image and an ultrasound image as follows, using an ultrasound transceiver having an ultrasound imaging region smaller than a radiography region. That is, the method moves the ultrasound transceiver to a retracted position outside the radiography region in a case in which a radiographic image is captured and moves the ultrasound transceiver in the radiography region in a case in which an ultrasound image is captured. In this case, the ultrasound transceiver does not need to be made of a material that transmits radiation. In addition, it is not necessary to increase the dose of radiation emitted from the radiation source. Further, it is not necessary to perform image processing for removing the image of the ultrasound transceiver from the radiographic image.

However, the above-mentioned method has a problem that the imaging time increases since the capture of the radiographic image and the capture of the ultrasound image are sequentially performed. In the mammography apparatus, since the breast is interposed between the compression plate and the imaging table and is then compressed, the long imaging time inflicts great pain on the subject whose breast is compressed. Therefore, an increase in the imaging time is a problem to be solved first in the mammography apparatus.

A first object of the technology according to the present disclosure is to provide a mammography apparatus that can reduce the imaging time of the breast, as compared to a case in which the capture of a radiographic image and the capture of an ultrasound image are sequentially performed, and a method for operating the mammography apparatus.

A second object of the technology according to the present disclosure is to provide an image processing apparatus that can simply generate a radiographic image without an image of an ultrasound transceiver, a program for operating the image processing apparatus, and a method for operating the image processing apparatus.

SUMMARY

In order to achieve the first object, according to the present disclosure, there is provided a mammography apparatus comprising: a radiation source that irradiates a breast with radiation; a radiation detector having a radiography region in which pixels that detect the radiation transmitted through the breast are two-dimensionally arranged; an ultrasound transceiver that is provided between the radiation source and the radiation detector and has an ultrasound imaging region which is smaller than the radiography region and in which ultrasound transducers that transmit ultrasonic waves to the breast and receive ultrasound echoes from the breast are arranged; a scanning mechanism that moves the ultrasound transceiver from a scanning start position to a scanning end position in the radiography region; and a control unit that directs the radiation source to emit the radiation in a plurality of states in which the ultrasound transceiver is disposed at different positions of the radiography region while the ultrasound transceiver is moved from the scanning start position to the scanning end position.

Preferably, the mammography apparatus further comprises a generation unit that generates a removed radiographic image, in which an image of the ultrasound transceiver has been removed, on the basis of a plurality of radiographic images of the breast in the plurality of states.

Preferably, the generation unit generates a plurality of cutout images obtained by cutting out a region other than the image of the ultrasound transceiver from the plurality of radiographic images and combines the plurality of cutout images to generate the removed radiographic image.

Preferably, the control unit directs the radiation source to emit the radiation only in a state in which the ultrasound transceiver is disposed in a region other than a set region. Preferably, in a case in which the radiography region is divided into a first region close to a chest wall and a second region away from the chest wall, the set region is set to the first region.

Preferably, the mammography apparatus further comprises: an imaging table in which the radiation detector is accommodated and on which the breast is placed; and a compression plate that is provided so as to face the imaging table and compresses the breast interposed between the compression plate and the imaging table. Preferably, the ultrasound transceiver is provided in the compression plate.

Preferably, the mammography apparatus further comprises an imaging table in which the radiation detector is accommodated and on which the breast is placed. Preferably, the ultrasound transceiver is provided in the imaging table.

Preferably, the mammography apparatus further comprises a shielding unit that shields irradiation of the radiation to the ultrasound transceiver.

Preferably, the shielding unit is an irradiation field limiter that sets an irradiation field of the radiation to the radiography region.

Preferably, the mammography apparatus has a tomosynthesis imaging function that moves the radiation source to a plurality of positions with respect to the radiation detector and directs the radiation source to emit the radiation at each position, and the plurality of radiographic images are projection images captured by the tomosynthesis imaging function.

According to the present disclosure, there is provided a method for operating a mammography apparatus comprising a radiation source that irradiates a breast with radiation, a radiation detector having a radiography region in which pixels that detect the radiation transmitted through the breast are two-dimensionally arranged, an ultrasound transceiver that is provided between the radiation source and the radiation detector and has an ultrasound imaging region which is smaller than the radiography region and in which ultrasound transducers that transmit ultrasonic waves to the breast and receive ultrasound echoes from the breast are arranged, a scanning mechanism that moves the ultrasound transceiver from a scanning start position to a scanning end position in the radiography region, and a control unit. The method comprises allowing the control unit to direct the radiation source to emit the radiation in a plurality of states in which the ultrasound transceiver is disposed at different positions of the radiography region while the ultrasound transceiver is moved from the scanning start position to the scanning end position.

In order to achieve the second object, according to the present disclosure, there is provided an image processing apparatus comprising: an acquisition unit that acquires a plurality of radiographic images in which an image of an ultrasound transceiver is disposed at different positions; and a generation unit that generates a removed radiographic image, in which the image of the ultrasound transceiver has been removed, on the basis of the plurality of radiographic images acquired by the acquisition unit.

Preferably, the generation unit generates a plurality of cutout images obtained by cutting out a region other than the image of the ultrasound transceiver from the plurality of radiographic images and combines the plurality of cutout images to generate the removed radiographic image.

According to the present disclosure, there is provided a program for operating an image processing apparatus. The program causes a computer to function as: an acquisition unit that acquires a plurality of radiographic images in which an image of an ultrasound transceiver is disposed at different positions; and a generation unit that generates a removed radiographic image, in which the image of the ultrasound transceiver has been removed, on the basis of the plurality of radiographic images acquired by the acquisition unit.

According to the present disclosure, there is provided a method for operating an image processing apparatus. The method comprises: an acquisition step of acquiring a plurality of radiographic images in which an image of an ultrasound transceiver is disposed at different positions; and a generation step of generating a removed radiographic image, in which the image of the ultrasound transceiver has been removed, on the basis of the plurality of radiographic images acquired in the acquisition step.

According to the technology of the present disclosure, it is possible to provide a mammography apparatus that can reduce the imaging time of the breast, as compared to a case in which the capture of a radiographic image and the capture of an ultrasound image are sequentially performed, and a method for operating the mammography apparatus.

In addition, according to the technology of the present disclosure, it is possible to provide an image processing apparatus that can simply generate a radiographic image without an image of an ultrasound transceiver, a program for operating the image processing apparatus, and a method for operating the image processing apparatus.

BRIEF DESCRIPTION OF THE DRAWINGS

Exemplary embodiments according to the technique of the present disclosure will be described in detail based on the following figures, wherein:

FIGS. 15A and 15B are diagrams illustrating a third embodiment in which radiation is shielded such that the ultrasound transceiver is not irradiated with the radiation, FIG. 15A illustrates a case in which the ultrasound transceiver is disposed at a scanning start position and FIG. 15B illustrates a case in which the ultrasound transceiver is disposed at a scanning end position;

FIG. 16 is a diagram illustrating a tomosynthesis imaging function according to a fourth embodiment;

DETAILED DESCRIPTION

First Embodiment

Figure 1:
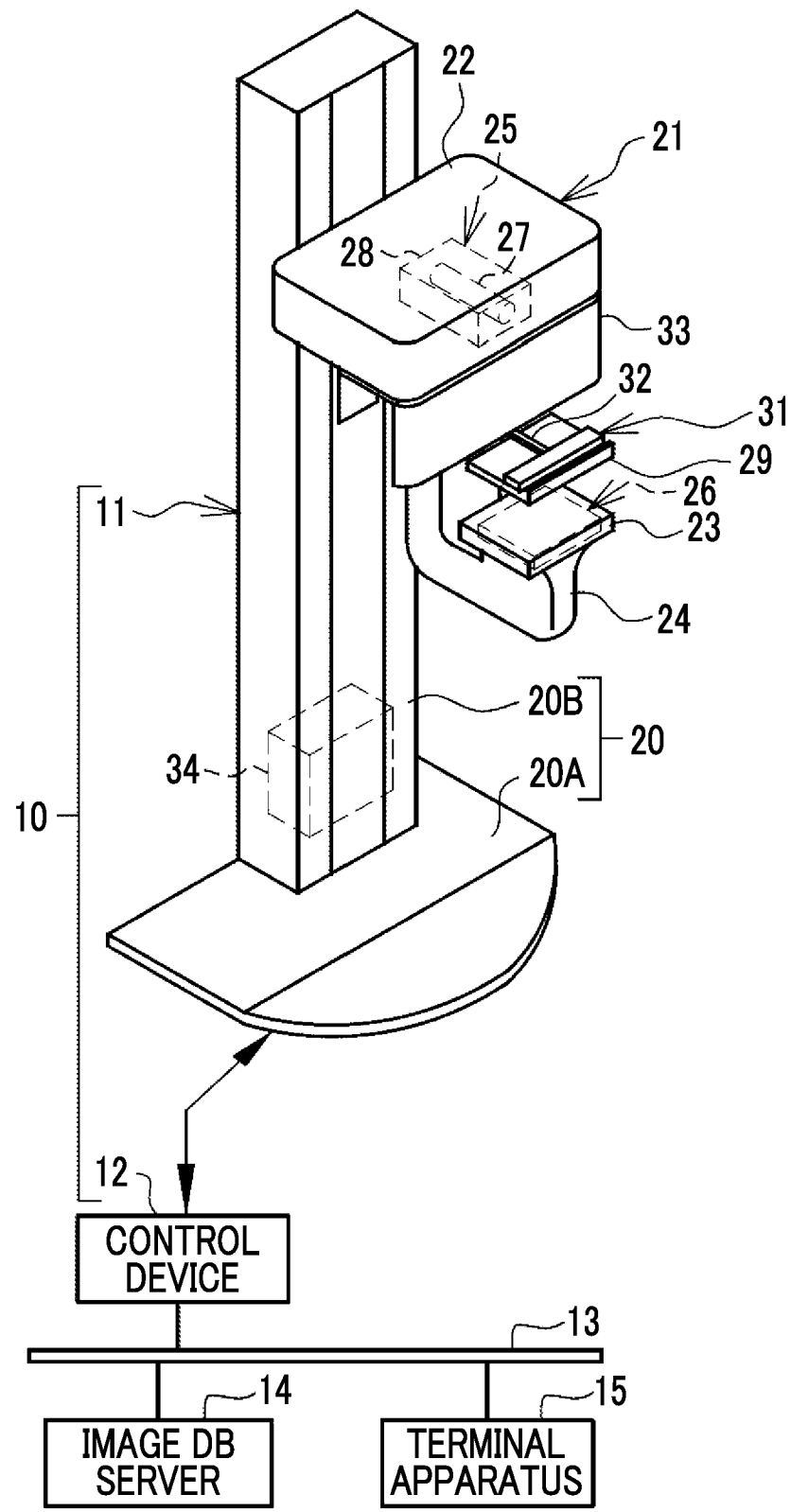
FIG. 1 is a diagram illustrating, for example, a mammography apparatus.
Figure 2:
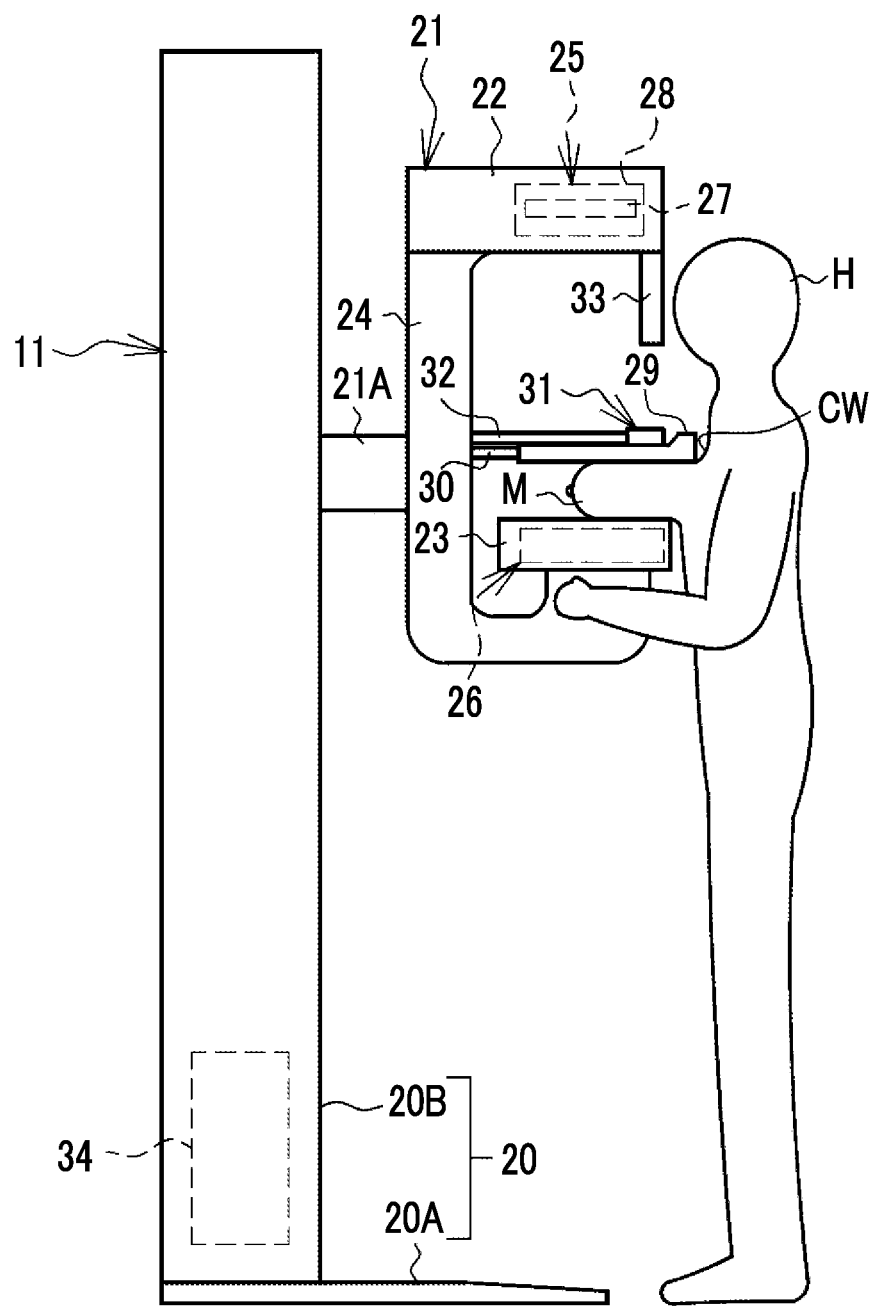
FIG. 2 is a diagram illustrating an apparatus main body of the mammography apparatus.

In FIGS. 1 and 2, a mammography apparatus 10 uses a breast M of a subject H as an object. The mammography apparatus 10 irradiates the breast M with radiation R (see FIG. 3), such as X-rays or γ-rays, to capture a radiographic image of the breast M. In addition, the mammography apparatus 10 transmits ultrasonic waves US (see FIG. 5) to the breast M, receives ultrasound echoes UE (see FIG. 5) from the breast M, and captures an ultrasound image (for example, a B-mode image) of the breast M. In the following description, in some cases, the capture of a radiographic image is referred to as radiography and the capture of an ultrasound image is referred to as ultrasound imaging.

The mammography apparatus 10 includes an apparatus main body 11 and a control device 12 corresponding to an image processing apparatus. The apparatus main body 11 is installed, for example, in a radiography room of a medical facility. The control device 12 is a computer, such as a personal computer or a workstation, and is installed, for example, in a control room next to the radiography room. The control device 12 is connected to an image database (hereinafter, referred to as DB) server 14 through a network 13, such as a local area network (LAN), such that it can communicate with the image DB server. The image DB server 14 receives a radiographic image and an ultrasound image from the mammography apparatus 10, and accumulates and manages the radiographic image and the ultrasound image.

A terminal apparatus 15 is also connected to the network 13. The terminal apparatus 15 is, for example, a personal computer that is used by a doctor to make a diagnosis based on the radiographic image and the ultrasound image. The terminal apparatus 15 receives the radiographic image and the ultrasound image from the image DB server 14 and displays the radiographic image and the ultrasound image on a display.

The apparatus main body 11 includes a stand 20 and an arm 21. The stand 20 includes a pedestal 20A that is provided on the floor of the radiography room and a support 20B that extends from the pedestal 20A in a height direction. The arm 21 has a substantially C-shape in a side view and is connected to the support 20B through a connection portion 21A. The arm 21 can be moved with respect to the support 20B in the height direction by the connection portion 21A and the height of the arm 21 can be adjusted according to the height of the subject H by the connection portion 21A. In addition, the arm 21 is rotatable on a rotation axis perpendicular to the support 20B through the connection portion 21A.

The arm 21 includes a radiation generation portion 22, an imaging table 23, and a main body portion 24. The radiation generation portion 22 accommodates a radiation source 25. The breast M is placed on the imaging table 23. In addition, the imaging table 23 accommodates a radiation detector 26. The main body portion 24 integrally connects the radiation generation portion 22 and the imaging table 23. The radiation generation portion 22 is provided on the upper side in the height direction and the imaging table 23 is provided on the lower side in the height direction at a posture where the imaging table 23 faces the radiation generation portion 22.

The radiation source 25 includes a radiation tube 27 and a housing 28 that accommodates the radiation tube 27. The radiation detector 26 detects the radiation R transmitted through the breast M and outputs a radiographic image.

A compression plate 29 is attached between the radiation generation portion 22 and the imaging table 23 in the main body portion 24. The compression plate 29 is made of a material that transmits the radiation R, the ultrasonic waves US, and the ultrasound echoes UE. The compression plate 29 is made of a resin, such as polymethylpentene, polycarbonate, acryl, or polyethylene terephthalate. In particular, polymethylpentene has low rigidity, high elasticity, and high flexibility. In addition, for polymethylpentene, acoustic impedance that affects the reflectivity of the ultrasonic waves US and the ultrasound echoes UE and an attenuation coefficient that affects the attenuation of the ultrasonic waves US and the ultrasound echoes UE are appropriate values. Therefore, polymethylpentene is suitable as the material forming the compression plate 29.

The compression plate 29 is provided so as to face the imaging table 23. The compression plate 29 can be moved in a direction toward the imaging table 23 and a direction away from the imaging table 23 by a movement mechanism 30. The compression plate 29 is moved to the imaging table 23 and compresses the breast M interposed between the compression plate 29 and the imaging table 23.

An ultrasound transceiver 31 is provided on a surface of the compression plate 29 which is close to the radiation generation portion 22. The ultrasound transceiver 31 can be moved in the direction toward the imaging table 23 and the direction away from the imaging table 23 by a scanning mechanism 32 in operative association with the movement of the compression plate 29. In addition, the ultrasound transceiver 31 is moved on the surface of the compression plate 29 which is close to the radiation generation portion 22 in a depth direction (a direction toward the subject H and a direction away from the subject H) by the scanning mechanism 32. The scanning mechanism 32 is made of a material that transmits the radiation R.

A face guard 33 is attached to a lower part of the front surface of the radiation generation portion 22. The face guard 33 protects the face of the subject H from the radiation R. In addition, letters CW indicate the chest wall of the subject H.

A voltage generator 34 that generates a tube voltage applied to the radiation tube 27 is provided in the support 20B. In addition, a voltage cable (not illustrated) that extends from the voltage generator 34 is provided in the support 20B. The voltage cable further extends from the connection portion 21A into the radiation generation portion 22 through the arm 21 and is connected to the radiation source 25.

Figure 3:
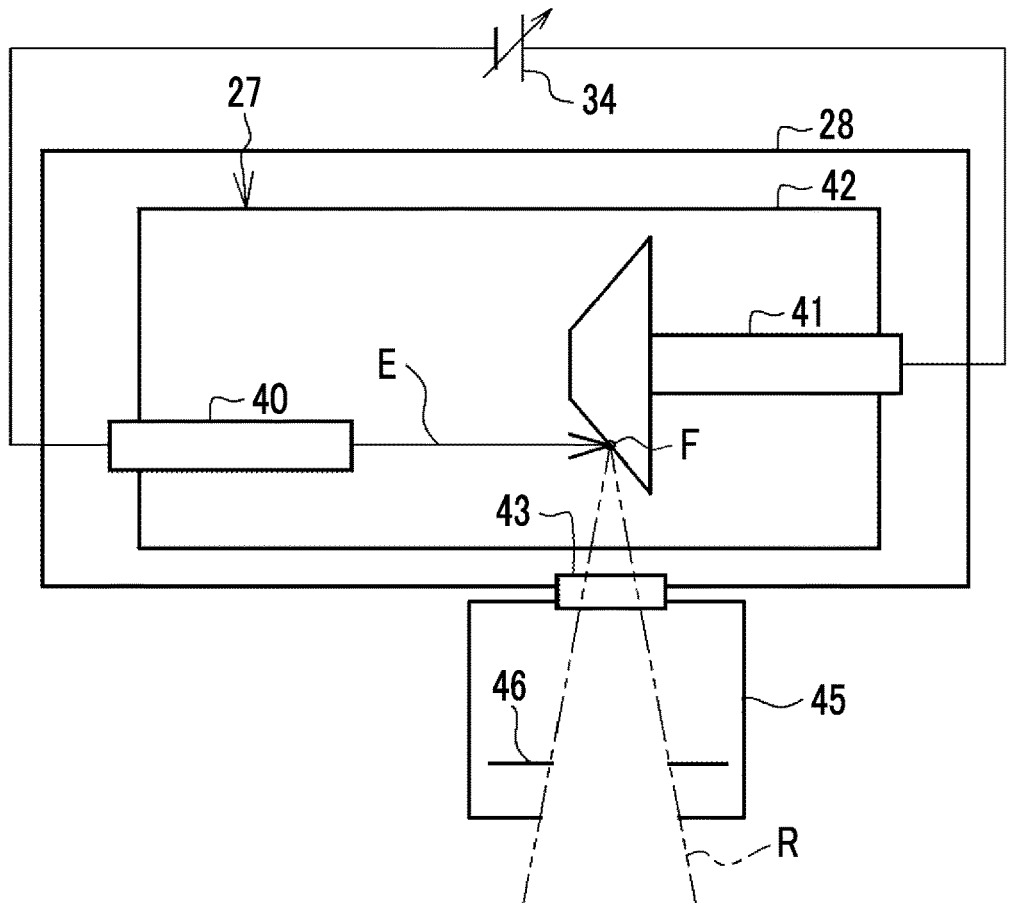
FIG. 3 is a diagram illustrating a radiation tube.

In FIG. 3, the radiation tube 27 includes a cathode 40 and an anode 41. The cathode 40 emits electrons E. The electrons E collide with the anode 41 and the anode 41 emits the radiation R. The cathode 40 and the anode 41 are accommodated in a vacuum glass tube 42. The anode 41 is a rotating anode that is rotated by a rotation mechanism.

The voltage generator 34 applies a tube voltage between the cathode 40 and the anode 41. The electrons E are emitted from the cathode 40 to the anode 41 by the application of the tube voltage. Then, the radiation R is emitted from a point (hereinafter, referred to as a focus) F of the anode 41 where the electrons E collides.

The housing 28 is provided with a radiation transmission window 43 that transmits the radiation R. The radiation R emitted from the anode 41 is emitted to the outside of the housing 28 through the radiation transmission window 43. In addition, the housing 28 is filled with insulating oil.

An irradiation field limiter 45 (not illustrated in FIGS. 1 and 2) is provided below the radiation transmission window 43 in the height direction. The irradiation field limiter 45 is also called a collimator and sets the irradiation field of the radiation R in a radiography region 55 (see FIG. 6) of the radiation detector 26. Specifically, the irradiation field limiter 45 includes a plurality of shielding plates 46 which are made of, for example, lead and shield the radiation R transmitted through the radiation transmission window 43. The shielding plates 46 are moved to change the size of, for example, a rectangular irradiation opening defined by the shielding plates 46 to set the irradiation field of the radiation R.

Figure 4:
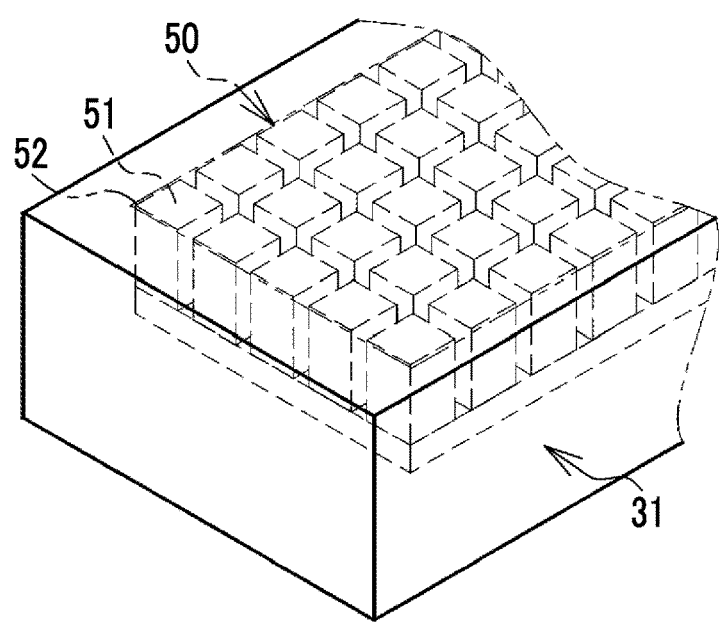
FIG. 4 is a diagram illustrating the internal structure of an ultrasound transceiver.

In FIG. 4 illustrating the ultrasound transceiver 31 as viewed from the radiation detector 26, the ultrasound transceiver 31 has an ultrasound transducer array 50. The ultrasound transducer array 50 is configured by two-dimensionally arranging a plurality of ultrasound transducers 51. As is well known, the ultrasound transducer 51 is configured by forming electrodes at both ends of a piezoelectric body, such as a piezoelectric ceramic typified by lead (Pb) zirconatetitanate (PZT) or a polymeric piezoelectric element typified by polyvinylidene difluoride (PVDF). An arrangement surface of the ultrasound transducers 51 defines an ultrasound imaging region 52 which captures an ultrasound image of the breast M.

Figure 5:
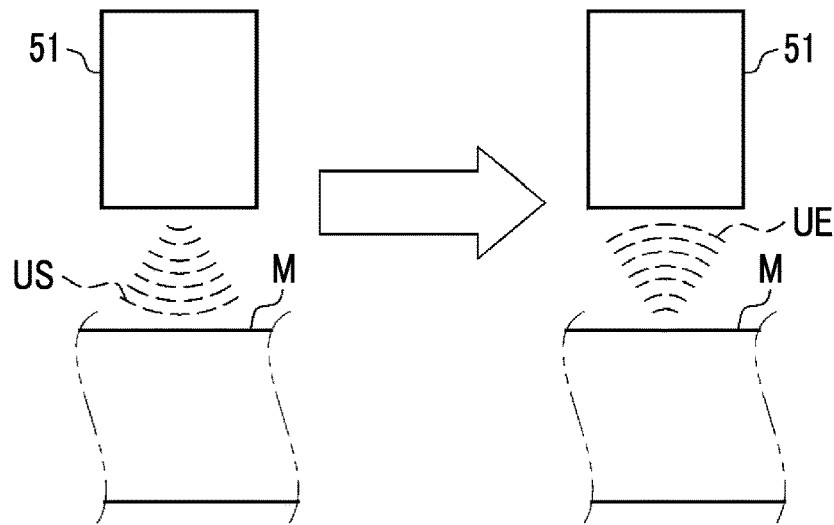
FIG. 5 is a diagram illustrating an aspect in which the ultrasound transducer transmits ultrasonic waves to the breast and receives ultrasound echoes from the breast.

As illustrated on the left side of an arrow in FIG. 5, the ultrasound transducer 51 transmits the ultrasonic waves US to the breast M. In addition, as illustrated on the right side of the arrow, the ultrasound transducer 51 receives the ultrasound echoes UE which are reflected waves of the ultrasonic waves US from the breast M. In FIG. 5, for example, the compression plate 29 is not illustrated for simplicity of illustration.

Figure 6:
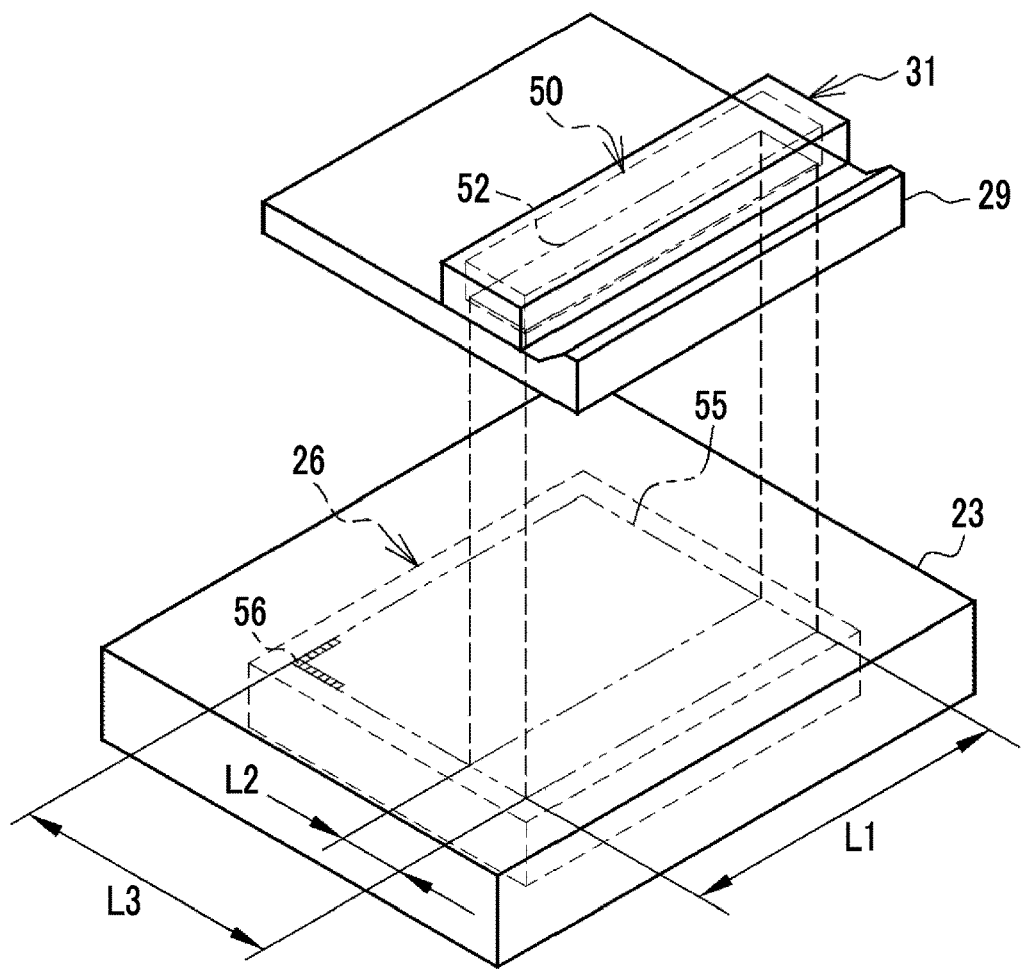
FIG. 6 is a diagram illustrating an imaging table and a compression plate.

In FIG. 6, the radiation detector 26 has the radiography region 55. The radiography region 55 is a region which detects the radiation R transmitted through the breast M and captures a radiographic image of the breast M. Specifically, the radiography region 55 is a region in which pixels 56 converting the radiation R into an electric signal (hereinafter, referred to as a radiographic image signal) are two-dimensionally arranged. The radiation detector 26 is referred to as a flat panel detector (FPD). The radiation detector 26 may be an indirect conversion type that includes, for example, a scintillator converting the radiation R into visible light and converts visible light emitted from the scintillator into a radiographic image signal or a direct conversion type that directly converts the radiation R into a radiographic image signal.

The long sides of the ultrasound imaging region 52 and the radiography region 55 have the same length L1. In contrast, a length L2 of a short side of the ultrasound imaging region 52 is less than a length L3 of a short side of the radiography region 55 and is, for example, a quarter of the length L3 of the short side of the radiography region 55. As such, the ultrasound imaging region 52 is smaller than the radiography region 55. In FIG. 6, for simplicity of illustration, for example, the scanning mechanism 32 and the main body portion 24 of the aim 21 are not illustrated.

For example, the mammography apparatus 10 captures the image of the breast M using two imaging methods, that is, a craniocaudal view (CC) imaging method and a mediolateral oblique view (MLO) imaging method. The CC imaging is an imaging method which captures an image while compressing the breast M interposed between the imaging table 23 and the compression plate 29 in the vertical direction. In contrast, the MLO imaging is an imaging method which captures an image while compressing the breast M interposed between the imaging table 23 and the compression plate 29 at an inclination angle of about 60°.

Figure 7:
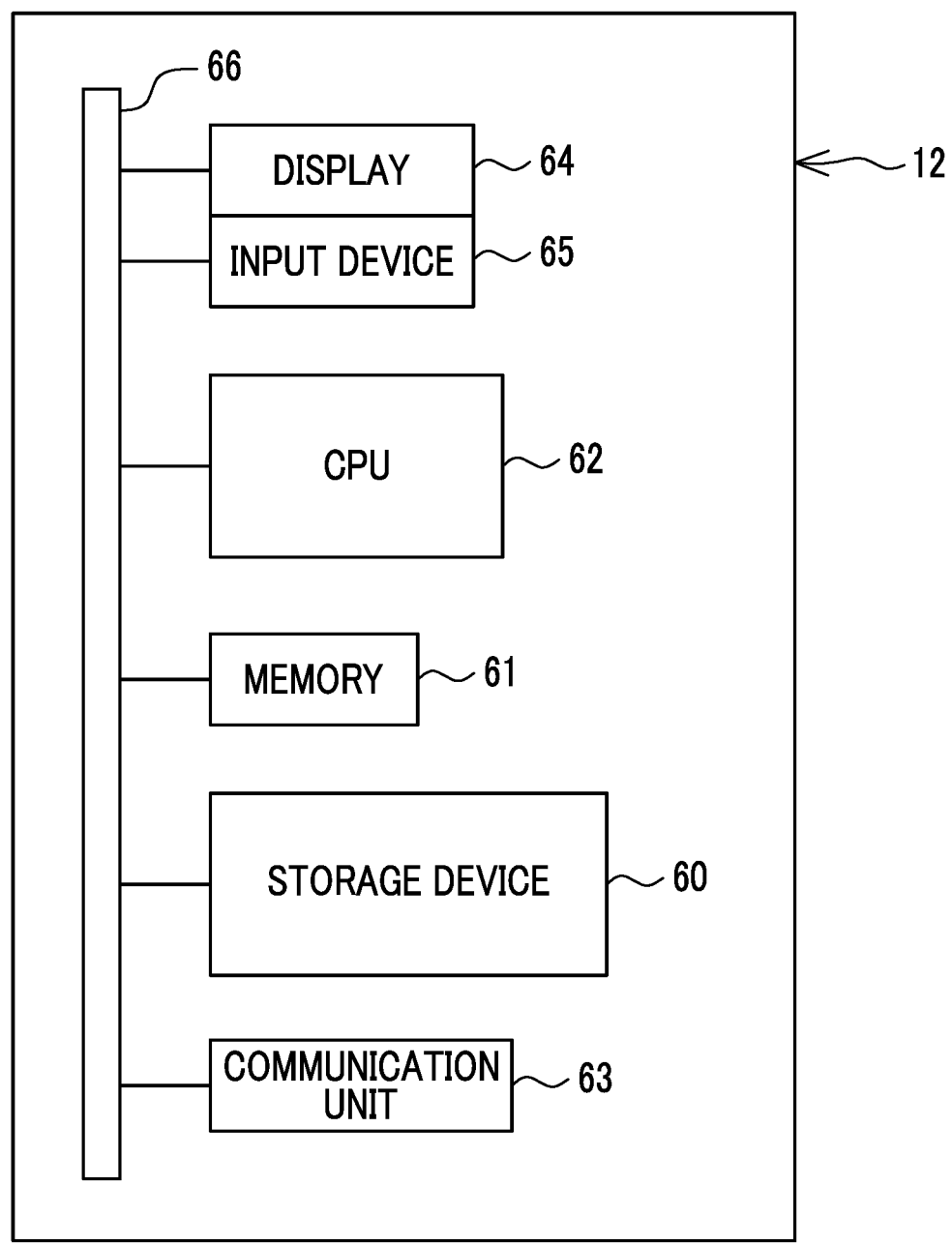
FIG. 7 is a block diagram illustrating a computer forming a control device.

In FIG. 7, a computer forming the control device 12 comprises a storage device 60, a memory 61, a central processing unit (CPU) 62 corresponding to a control unit, a communication unit 63, a display 64, and an input device 65. These components are connected to each other through a data bus 66.

The storage device 60 is a hard disk drive that is provided in the computer forming the control device 12 or is connected to the computer through a cable or a network. Alternatively, the storage device 60 is a disk array formed by connecting a plurality of hard disk drives. The storage device 60 stores a control program, such as an operating system, various application programs, and various types of data associated with these programs.

The memory 61 is a work memory that is used by the CPU 62 to perform processes. The CPU 62 loads the program stored in the storage device 60 to the memory 61 and performs the process based on the program to control the overall operation of each unit of the computer.

The communication unit 63 is a network interface that controls the transmission of various kinds of information through the network 13. The display 64 displays various screens. The various screens have an operation function by a graphic user interface (GUI). The computer forming the control device 12 receives the input of an operation command from the input device 65 through various screens. The input device 65 is, for example, a keyboard, a mouse, and a touch panel.

Figure 8:
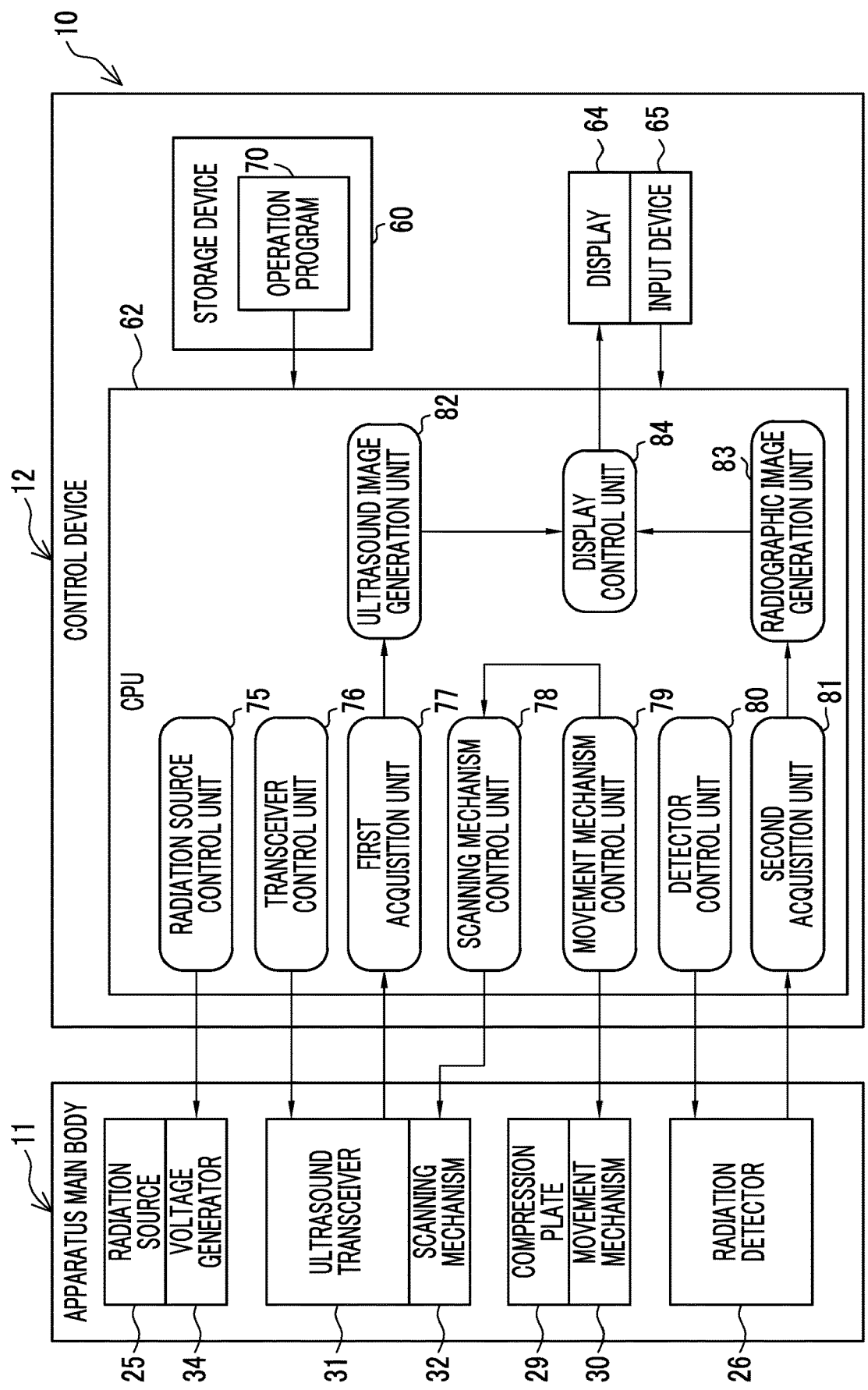
FIG. 8 is a block diagram illustrating each processing unit of a CPU of the control device.

In FIG. 8, an operation program 70 is stored as an application program in the storage device 60 of the control device 12. The operation program 70 is an application program that causes the computer forming the control device 12 to function as an image processing apparatus.

In a case in which the operation program 70 starts, the CPU 62 of the computer forming the control device 12 functions as a radiation source control unit 75, a transceiver control unit 76, a first acquisition unit 77, a scanning mechanism control unit 78, a movement mechanism control unit 79, a detector control unit 80, a second acquisition unit 81 corresponding to an acquisition unit, an ultrasound image generation unit 82, a radiographic image generation unit 83 corresponding to a generation unit, and a display control unit 84 in cooperation with, for example, the memory 61.

The radiation source control unit 75 controls the operation of the voltage generator 34 to control the operation of the radiation source 25. Specifically, the radiation source control unit 75 sets the irradiation conditions of the radiation R input through the input device 65 to the voltage generator 34. The irradiation conditions include the tube voltage applied from the voltage generator 34 to the radiation tube 27, a tube current, and the irradiation time of the radiation R. Each value of the irradiation conditions is adjusted such that the density of the radiographic image is at a substantially constant level regardless of an individual difference in the breast M. Instead of the tube current and the irradiation time, a tube current-irradiation time product (so-called mAs value) may be used as the irradiation conditions.

In addition, the radiation source control unit 75 controls the irradiation field limiter 45 such that the shielding plate 46 of the irradiation field limiter 45 is moved to set the irradiation field.

The transceiver control unit 76 controls the operation of the ultrasound transceiver 31. The transceiver control unit 76 controls the transmission timing of the ultrasonic waves US from each ultrasound transducer 51 such that a plurality of ultrasound transducers 51 of the ultrasound transceiver 31 sequentially transmit the ultrasonic waves US to the breast M. In addition, the transceiver control unit 76 directs each ultrasound transducer 51 to receive the ultrasound echoes UE and to output an electric signal (hereinafter, referred to as an ultrasound image signal) corresponding to the received ultrasound echoes UE to the first acquisition unit 77.

The first acquisition unit 77 acquires the ultrasound image signal output from the ultrasound transceiver 31. The ultrasound image signal is a signal that is the source of an ultrasound image. Therefore, the first acquisition unit 77 acquires the ultrasound image signal to substantially acquire an ultrasound image. The first acquisition unit 77 outputs the acquired ultrasound image signal to the ultrasound image generation unit 82.

The scanning mechanism control unit 78 controls the operation of the scanning mechanism 32. The scanning mechanism control unit 78 operates the scanning mechanism 32 in operative association with the movement of the compression plate 29 by the movement mechanism 30 to move the ultrasound transceiver 31 in the direction toward the imaging table 23 and the direction away from the imaging table 23. In addition, the scanning mechanism control unit 78 operates the scanning mechanism 32 such that the ultrasound transceiver 31 is moved for scanning on the surface of the compression plate 29 which is close to the radiation generation portion 22 in the depth direction. In the scanning process, the transceiver control unit 76 directs the ultrasound transducer 51 to transmit the ultrasonic waves US, to receive the ultrasound echoes UE, and to output an ultrasound image signal.

The movement mechanism control unit 79 controls the operation of the movement mechanism 30. Specifically, the movement mechanism control unit 79 operates the movement mechanism 30 to move the compression plate 29 in the direction toward the imaging table 23 and the direction away from the imaging table 23.

The movement mechanism 30 is provided with a pressure sensor (not illustrated) that measures the compression force of the compression plate 29 against the breast M. The compression force measured by the pressure sensor is input to the movement mechanism control unit 79. The movement mechanism control unit 79 moves the compression plate 29 such that the compression force falls within a prescribed range.

The detector control unit 80 controls the operation of the radiation detector 26. The detector control unit 80 directs the pixels 56 of the radiation detector 26 to start to accumulate charge which is the source of a radiographic image signal in synchronization with the irradiation start timing of the radiation R from the radiation source 25. In addition, the detector control unit 80 reads the accumulated charge from the pixels 56 in synchronization with the irradiation end timing of the radiation R from the radiation source 25 and outputs the charge as a radiographic image signal to the second acquisition unit 81.

The second acquisition unit 81 acquires the radiographic image signal output from the radiation detector 26. The radiographic image signal is a signal which is the source of a radiographic image. Therefore, the second acquisition unit 81 acquires the radiographic image signal to substantially acquire a radiographic image. The second acquisition unit 81 outputs the acquired radiographic image signal to the radiographic image generation unit 83.

The ultrasound image generation unit 82 generates an ultrasound image on the basis of the ultrasound image signal from the first acquisition unit 77. The ultrasound image generation unit 82 outputs the generated ultrasound image to the display control unit 84. Similarly, the radiographic image generation unit 83 generates a radiographic image on the basis of the radiographic image signal from the second acquisition unit 81 and outputs the generated radiographic image to the display control unit 84.

The display control unit 84 performs control such that various screens are displayed on the display 64. Specifically, the display control unit 84 performs control such that, for example, an irradiation condition input screen (not illustrated) for receiving the input of the irradiation conditions of the radiation R and an image display screen 95 (see FIG. 11) for displaying the ultrasound image from the ultrasound image generation unit 82 and the radiographic image from the radiographic image generation unit 83 side by side are displayed on the display 64.

Figure 9:
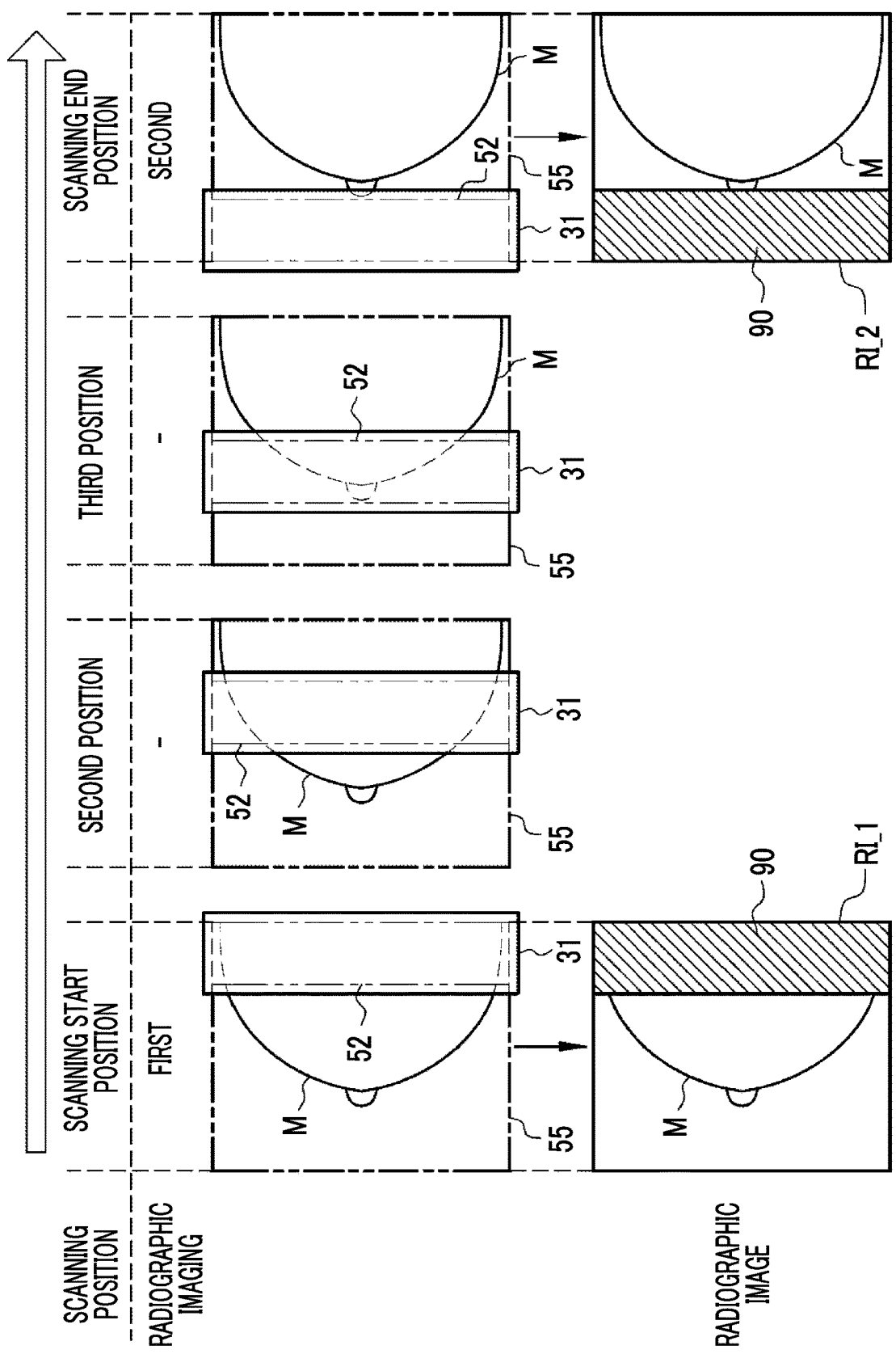
FIG. 9 is a diagram illustrating the scanning position and radiography timing of the ultrasound transceiver.

As illustrated in FIG. 9, the scanning mechanism control unit 78 operates the scanning mechanism 32 to move the ultrasound transceiver 31 to a total of four positions, that is, a scanning start position, a second position, a third position, and a scanning end position in this order. The transceiver control unit 76 directs the ultrasound transceiver 31 to transmit the ultrasonic waves US and to receive the ultrasound echoes UE at each of the positions. The first acquisition unit 77 outputs the ultrasound image signal output from the ultrasound transceiver 31 at each position to the ultrasound image generation unit 82 whenever the ultrasound image signal is output. The ultrasound image generation unit 82 connects the ultrasound image signals at each position to generate one ultrasound image.

The scanning start position is a position where the ultrasound transceiver 31 is closest to the chest wall CW and the ultrasound imaging region 52 covers a quarter of the radiography region 55 which is close to the chest wall CW. The second position is a position where the ultrasound transceiver 31 is moved in the depth direction by the length L2 of the short side of the ultrasound imaging region 52 from the scanning start position. Similarly, the third position is a position where the ultrasound transceiver 31 is moved in the depth direction by the length L2 from the second position. The scanning end position is a position where the ultrasound transceiver 31 is moved in the depth direction by the length L2 from the third position. The scanning end position is a position where the ultrasound transceiver 31 is furthest away from the chest wall CW.

As described with reference to FIG. 6, the length L2 of the short side of the ultrasound imaging region 52 is a quarter of the length L3 of the short side of the radiography region 55. Therefore, the transmission of the ultrasonic waves US and the reception of the ultrasound echoes UE by the ultrasound transceiver 31 are performed at each position that is away from an adjacent position by a distance corresponding to the length L2 to scan the entire region which has almost the same size as the radiography region 55 and has almost the same positional relationship with the breast M as the radiography region 55.

The radiation source control unit 75 directs the radiation source 25 to emit the radiation R in a plurality of states in which the ultrasound transceiver 31 is disposed at different positions of the radiography region 55 while the ultrasound transceiver 31 is moved from the scanning start position to the scanning end position by the scanning mechanism 32.

In FIG. 9, a state in which the ultrasound transceiver 31 is disposed at the scanning start position and the scanning end position corresponds to the state in which the ultrasound transceiver 31 is disposed at different positions of the radiography region 55. Therefore, the radiation source control unit 75 directs the radiation source 25 to emit the radiation R in the state in which the ultrasound transceiver 31 is disposed at the scanning start position (first radiography operation). In addition, the radiation source control unit 75 directs the radiation source 25 to emit the radiation R in the state in which the ultrasound transceiver 31 is disposed at the scanning end position (second radiography operation).

A radiographic image RI_1 is a radiographic image which is based on the radiographic image signal acquired by the second acquisition unit 81 in the first radiography operation. A radiographic image RI_2 is a radiographic image which is based on the radiographic image signal acquired by the second acquisition unit 81 in the second radiography operation. The radiographic image RI_1 includes an image 90 of the ultrasound transceiver 31 disposed at a position closest to the chest wall CW. The radiographic image RI_2 includes the image 90 of the ultrasound transceiver 31 disposed at a position that is furthest away from the chest wall CW and is symmetric to the position in the radiographic image RI_1. The radiographic images RI_1 and RI_2 correspond to a plurality of radiographic images in which the image 90 of the ultrasound transceiver 31 is disposed at different positions.

Figure 10:
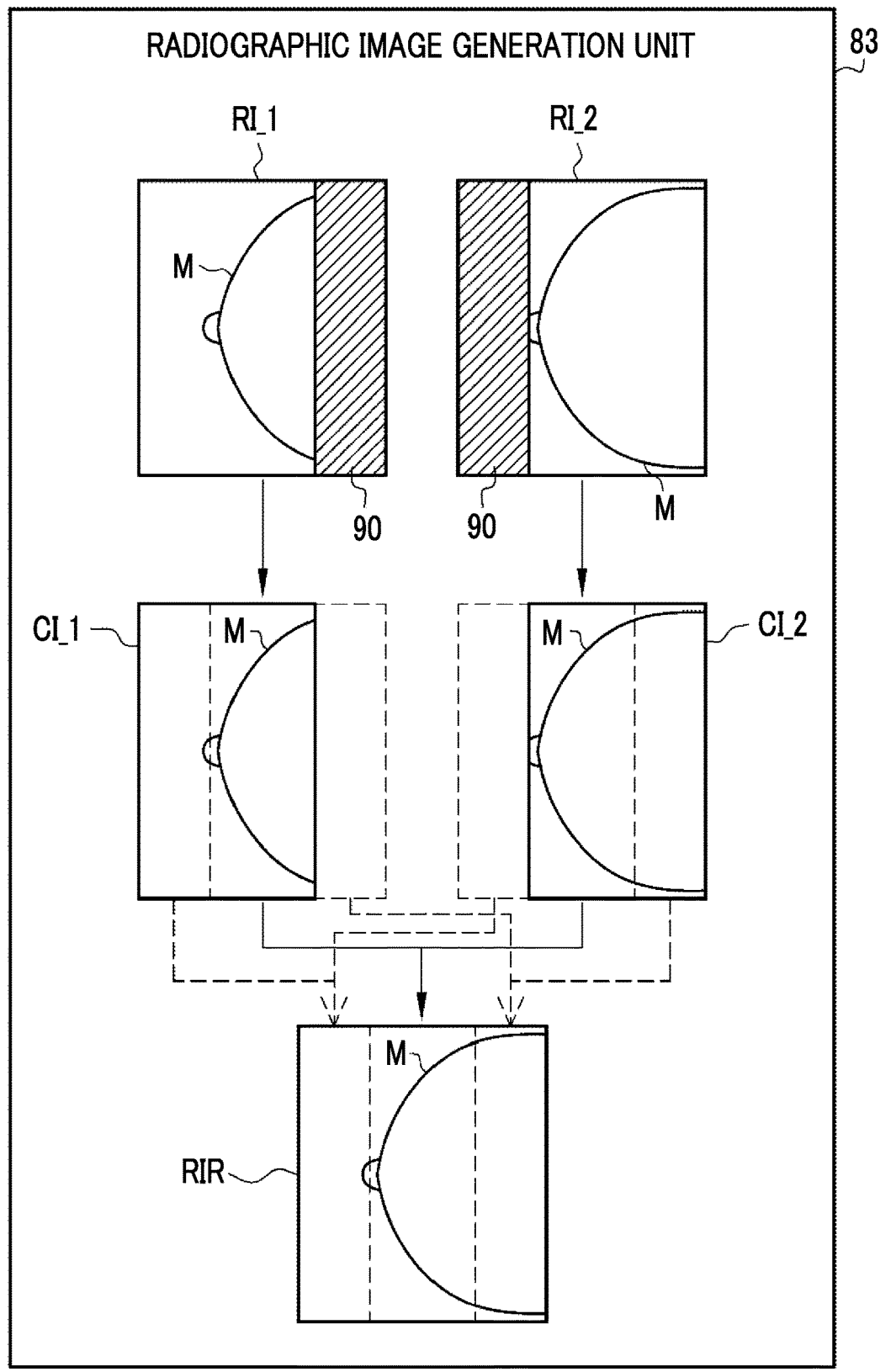
FIG. 10 is a diagram illustrating an aspect in which a radiographic image generation unit generates a removed radiographic image.

As illustrated in FIG. 10, the radiographic image generation unit 83 generates a removed radiographic image RIR, in which the image 90 of the ultrasound transceiver 31 disposed at different positions in a plurality of radiographic images RI_K (K=1 to N, N is the sum of a plurality of radiographic images, here N=2) acquired by the second acquisition unit 81 has been removed, on the basis of the plurality of radiographic images RI_K.

Specifically, the radiographic image generation unit 83 cuts out regions other than the image 90 of the ultrasound transceiver 31 from the radiographic images RI_1 and RI_2 to generate cutout images CI_1 and CI_2. That is, the region other than the image 90 of the ultrasound transceiver 31 is a region including the breast M in the radiographic images RI_1 and RI_2.

The radiographic image generation unit 83 recognizes the region of the image 90 of the ultrasound transceiver 31 included in each of the radiographic images RI_1 and RI_2 using a known image recognition technique. Then, the radiographic image generation unit 83 removes the recognized region from each of the radiographic images RI_1 and RI_2 to generate the cutout images CI_1 and CI_2.

In addition, instead of using the image recognition technique, the region of the image 90 of the ultrasound transceiver 31 included in each radiographic image RI_K may be stored as information in advance and the cutout image CI_K may be generated on the basis of the stored information. However, in this case, since the size of the image 90 changes depending on the distance between the imaging table 23 and the compression plate 29 (the size of the image 90 becomes smaller as the distance between the imaging table 23 and the compression plate 29 becomes longer and becomes larger as the distance between the imaging table 23 and the compression plate 29 becomes shorter), the region of the image 90 corresponding to the distance between the imaging table 23 and the compression plate 29 is stored. Alternatively, only one region of the image 90 corresponding to a given distance may be stored and the region may be multiplied by an enlargement ratio or a reduction ratio corresponding to the distance between the imaging table 23 and the compression plate 29 to adjust the size of the region.

The radiographic image generation unit 83 combines the generated cutout images CI_1 and CI_2 to generate the removed radiographic image RIR. In a case in which the cutout images CI_1 and CI_2 are combined with each other, the outline of the breast M included in each of the images C_1 and CI_2 is extracted by a known outline extraction technique. Then, the images CI_1 and CI_2 are combined such that the extracted outlines are matched with each other.

Figure 11:
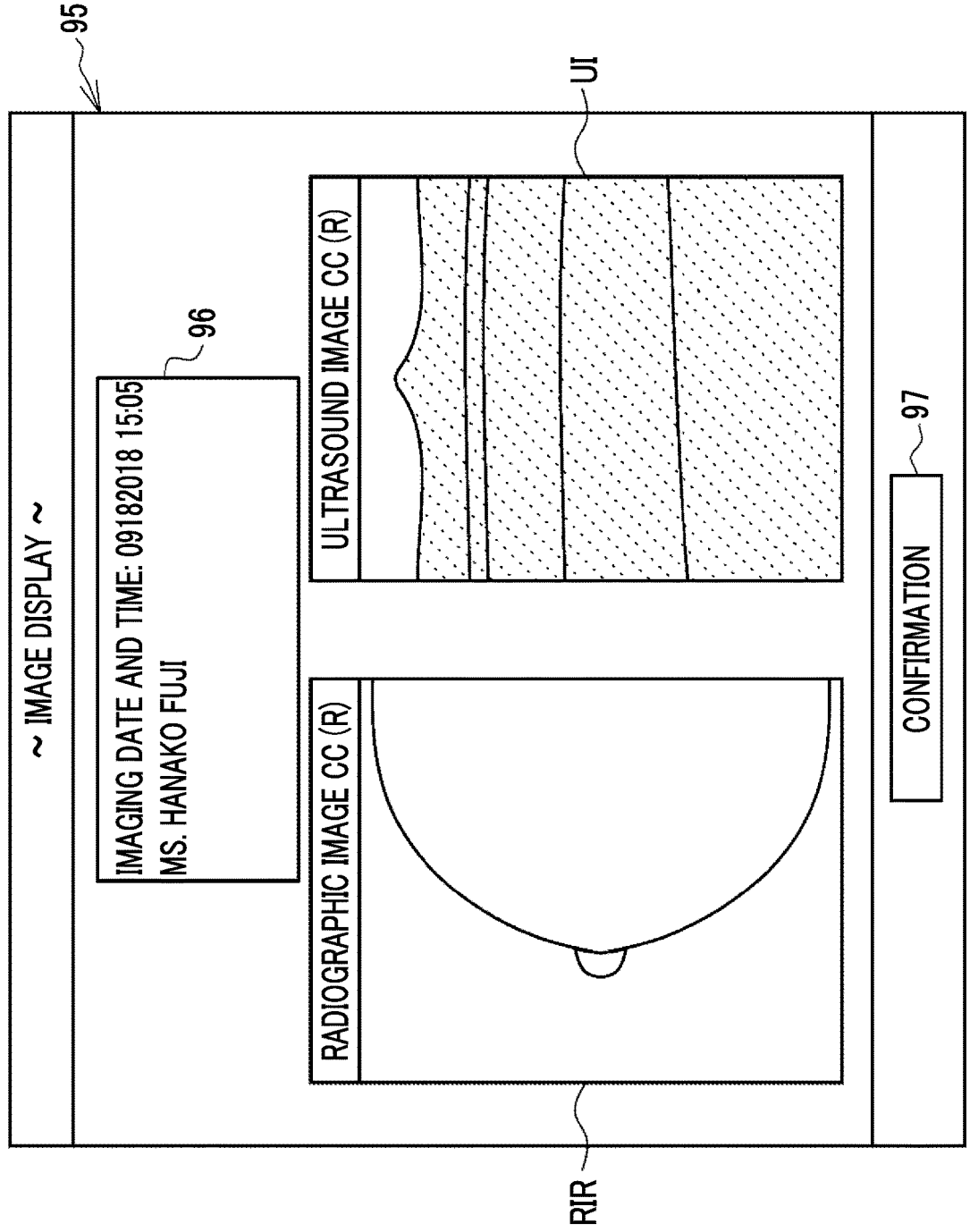
FIG. 11 is a diagram illustrating an image display screen.

The display control unit 84 displays the removed radiographic image RIR generated by the radiographic image generation unit 83 and the ultrasound image UI generated by the ultrasound image generation unit 82 side by side on the display 64 as illustrated in an image display screen 95 of FIG. 11. It is possible to display the display tomographic planes of the ultrasound image UI on the image display screen 95 such that the display tomographic planes are switched. In addition, reference numeral 96 indicates an information display region in which information related to imaging, such as the imaging date and time or the name of the subject H is displayed. Further, reference numeral 97 indicates a confirmation button for turning off the image display screen 95. Furthermore, "CC(R)" in each of the images RIR and UI indicates that each of the images RIR and UI is obtained by capturing an image of the right breast M using the CC imaging method.

The control device 12 transmits the ultrasound image UI generated by the ultrasound image generation unit 82 and the removed radiographic image RIR generated by the radiographic image generation unit 83 to the image DB server 14 through the communication unit 63.

Figure 12:
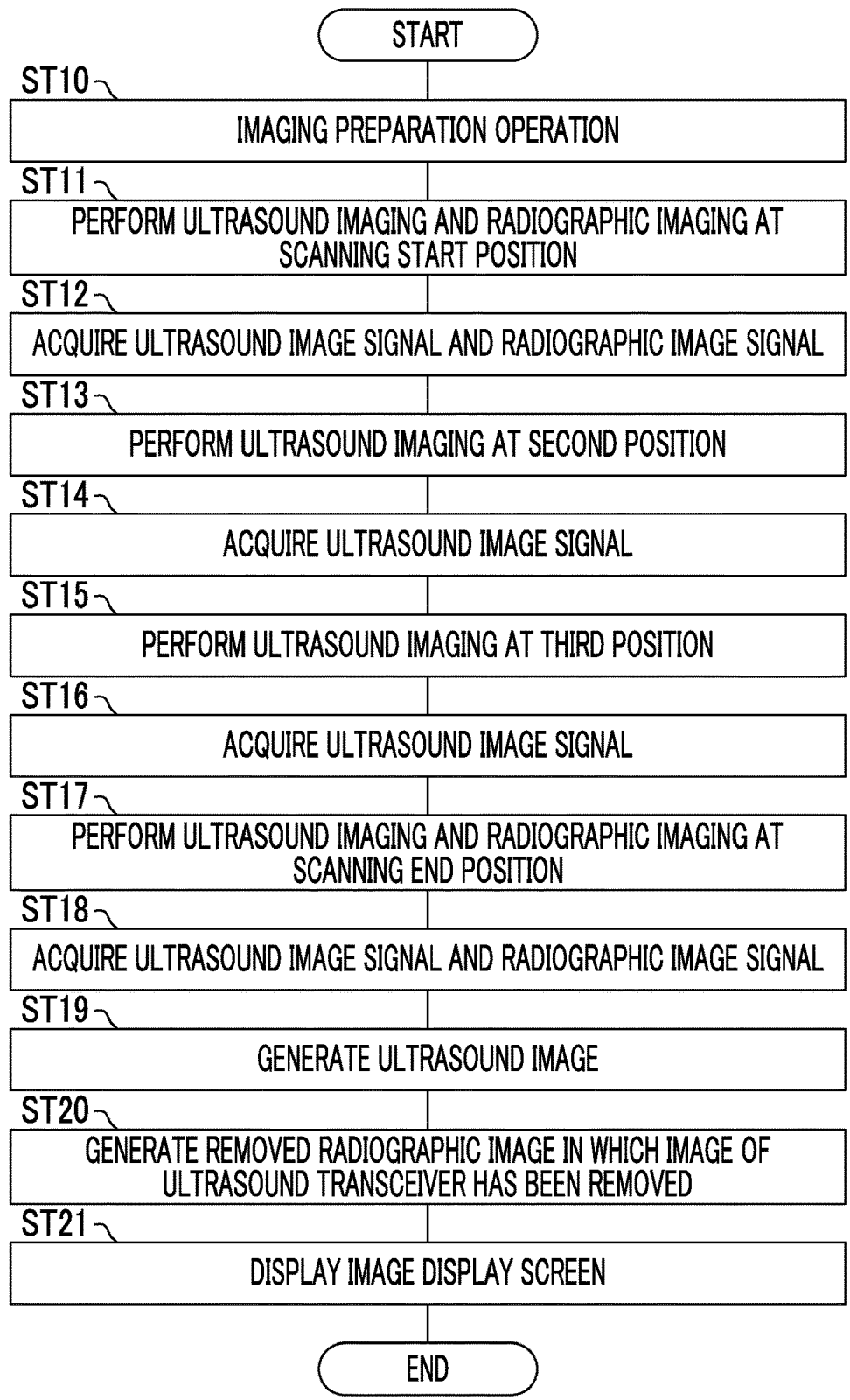
FIG. 12 is a flowchart illustrating the procedure of capturing an image of the breast in the mammography apparatus.

Next, the operation of the above-mentioned configuration will be described with reference to a flowchart illustrated in FIG. 12. The procedure of capturing the image of the breast M by the mammography apparatus 10 starts from an imaging preparation operation in Step ST10. The imaging preparation operation is performed by a radiology technician who operates the mammography apparatus 10 and is mainly related to the positioning of the breast M. For example, the imaging preparation operation is performed to guide the subject H in front of the apparatus main body 11 such that the breast M is placed on the imaging table 23. The imaging preparation operation includes an operation in which the movement mechanism 30 moves the compression plate 29 to the imaging table 23 to compress the breast M interposed between the compression plate 29 and the imaging table 23 under control of the movement mechanism control unit 79. After the imaging preparation operation ends, the radiology technician inputs a command to start imaging.

As illustrated in FIG. 9, first, at the scanning start position, the transceiver control unit 76 operates the ultrasound transceiver 31 to capture an ultrasound image of the breast M. In addition, the radiation source control unit 75 and the detector control unit 80 operate the radiation source 25 and the radiation detector 26 to capture a radiographic image of the breast M (Step ST11). Then, the first acquisition unit 77 acquires an ultrasound image signal from the ultrasound transceiver 31 and the second acquisition unit 81 acquires a radiographic image signal from the radiation detector 26 (Step ST12, an acquisition step).

Then, the scanning mechanism 32 moves the ultrasound transceiver 31 to the second position under the control of the scanning mechanism control unit 78. Then, ultrasound imaging is performed at the second position (Step ST13). Then, the first acquisition unit 77 acquires an ultrasound image signal (Step ST14). Similarly, the ultrasound transceiver 31 is moved to the third position and ultrasound imaging is performed at the third position (Step ST15). Then, the first acquisition unit 77 acquires an ultrasound image signal (Step ST16).

Finally, the scanning mechanism 32 moves the ultrasound transceiver 31 to the scanning end position under the control of the scanning mechanism control unit 78. Then, ultrasound imaging is performed at the scanning end position and radiography is performed (Step ST17). Then, similarly to Step ST12, the first acquisition unit 77 acquires an ultrasound image signal from the ultrasound transceiver 31 and the second acquisition unit 81 acquires a radiographic image signal from the radiation detector 26 (Step ST18, an acquisition step).

The ultrasound image signals acquired by the first acquisition unit 77 in Steps ST12, ST14, ST16, and ST18 are output to the ultrasound image generation unit 82. Then, the ultrasound image generation unit 82 generates an ultrasound image UI from the ultrasound image signals (Step ST19). The generated ultrasound image UI is output to the display control unit 84.

The radiographic image signals acquired by the second acquisition unit 81 in Steps ST12 and ST18 are output to the radiographic image generation unit 83. The radiographic image generation unit 83 generates the removed radiographic image RIR, in which the image 90 of the ultrasound transceiver 31 has been removed, on the basis of a plurality of radiographic images RI_K in which the images 90 of the ultrasound transceiver 31 are disposed at different positions as illustrated in FIG. 10 (Step ST20, a generation step).

Specifically, the radiographic image generation unit 83 generates a plurality of cutout images CI_K obtained by cutting out regions other than the image 90 of the ultrasound transceiver 31 from the plurality of radiographic images RI_K and combines the plurality of cutout images CI_K to generate the removed radiographic image RIR. The generated removed radiographic image RIR is output to the display control unit 84.

As illustrated in FIG. 11, the ultrasound image UI and the removed radiographic image RIR are displayed side by side on the display 64 by the display control unit 84 and are viewed by a radiology technician (Step ST21). In this way, one radiography and ultrasound imaging operation which is performed in a state in which the same breast M of the same subject H is compressed by the imaging table 23 and the compression plate 29 ends.

As described above, in this embodiment, the ultrasound transceiver 31 having the ultrasound imaging region 52 smaller than the radiography region 55 is used. The ultrasound transceiver 31 is moved for scanning from the scanning start position to the scanning end position by the scanning mechanism 32 and performs the transmission of the ultrasonic waves US to the breast M and the reception of the ultrasound echoes UE from the breast M, that is, ultrasound imaging for the breast M during the scanning. In addition, during the scanning, in a plurality of states in which the ultrasound transceiver 31 is disposed at different positions of the radiography region 55, the radiation source 25 emits the radiation R to perform radiography for the breast M. Therefore, it is possible to reduce the imaging time of the breast M and to ease the pain of the subject H, as compared to a case in which radiography and ultrasound imaging are sequentially performed.

In this embodiment, the second acquisition unit 81 acquires a plurality of radiographic images RI_K of the breast M captured by a plurality of radiography operations. Then, the radiographic image generation unit 83 generates the removed radiographic image RIR obtained by removing the image 90 of the ultrasound transceiver 31 disposed at different positions in the plurality of radiographic images RI_K on the basis of the plurality of radiographic images RI_K acquired by the second acquisition unit 81. The removed radiographic image RIR is generated by cutting out a region other than the image 90 of the ultrasound transceiver 31 from each of the plurality of radiographic images RI_K to generate a plurality of cutout images CI_K and combining the cutout images CI_K. Therefore, it is possible to simply generate a radiographic image in which the image 90 of the ultrasound transceiver 31 is not included.

In this embodiment, the ultrasound transceiver 31 is provided in the compression plate 29. Therefore, it is possible to reduce the amount of radiation emitted to a portion of the breast M shielded by the ultrasound transceiver 31.

Figure 13:
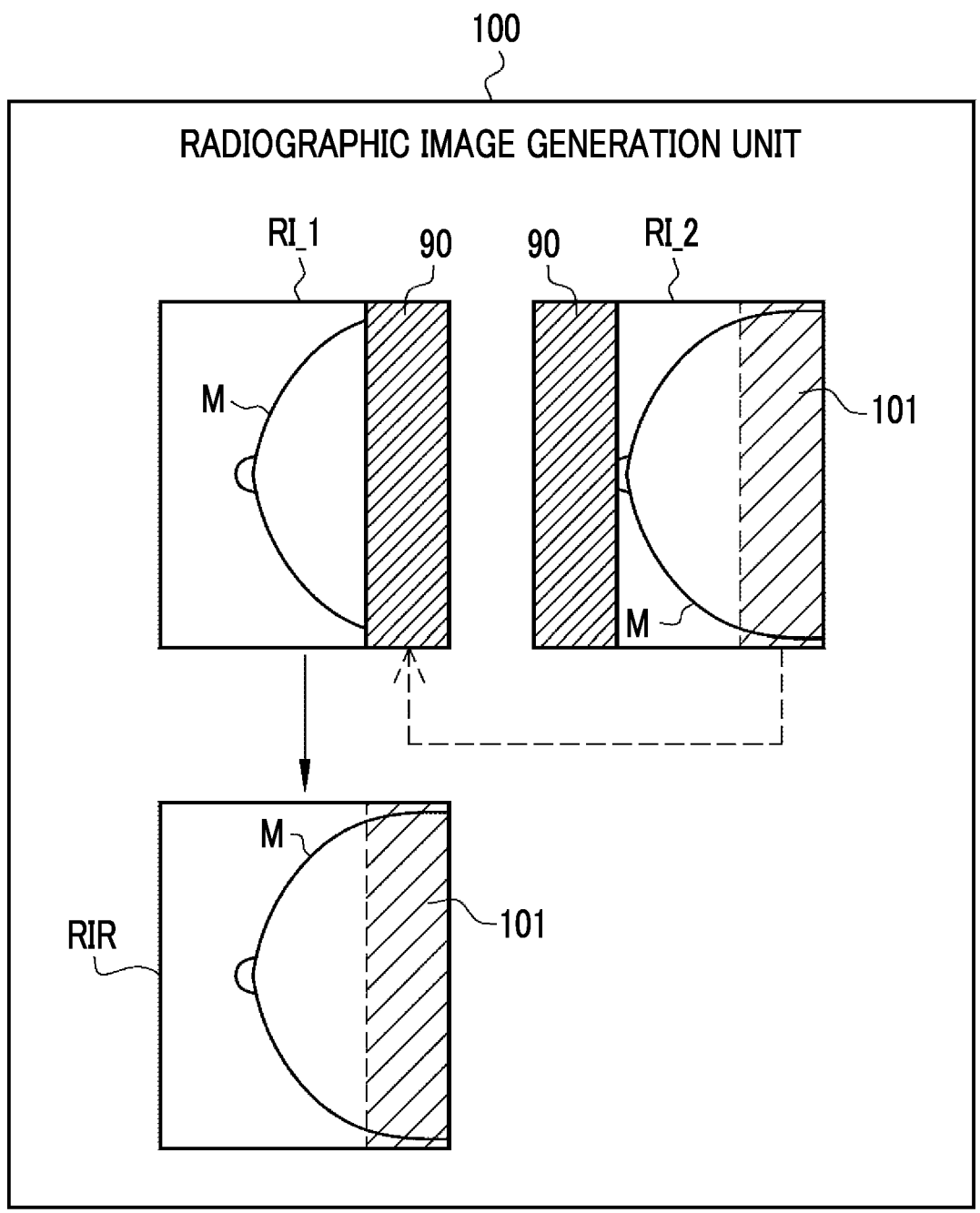
FIG. 13 is a diagram illustrating another example in which the radiographic image generation unit generates the removed radiographic image.

In addition, the removed radiographic image RIR may be generated by a method illustrated in FIG. 13. That is, the radiographic image generation unit 100 inserts, into a portion of the radiographic image RI_1 in which the image 90 of the ultrasound transceiver 31 is included, an image 101 of a portion of the radiographic image RI_2 corresponding to the portion to generate the removed radiographic image RIR. Conversely, the image of a portion of the radiographic image RI_1 corresponding to a portion of the radiographic image RI_2 in which the image 90 of the ultrasound transceiver 31 is included may be inserted into the portion of the radiographic image RI_2 generate the removed radiographic image RIR. As such, a method for generating the removed radiographic image RIR is not limited to the method illustrated in FIG. 10 which generates the plurality of cutout images CI_K and combines the plurality of cutout images CI_K.

Second Embodiment

Figure 14:
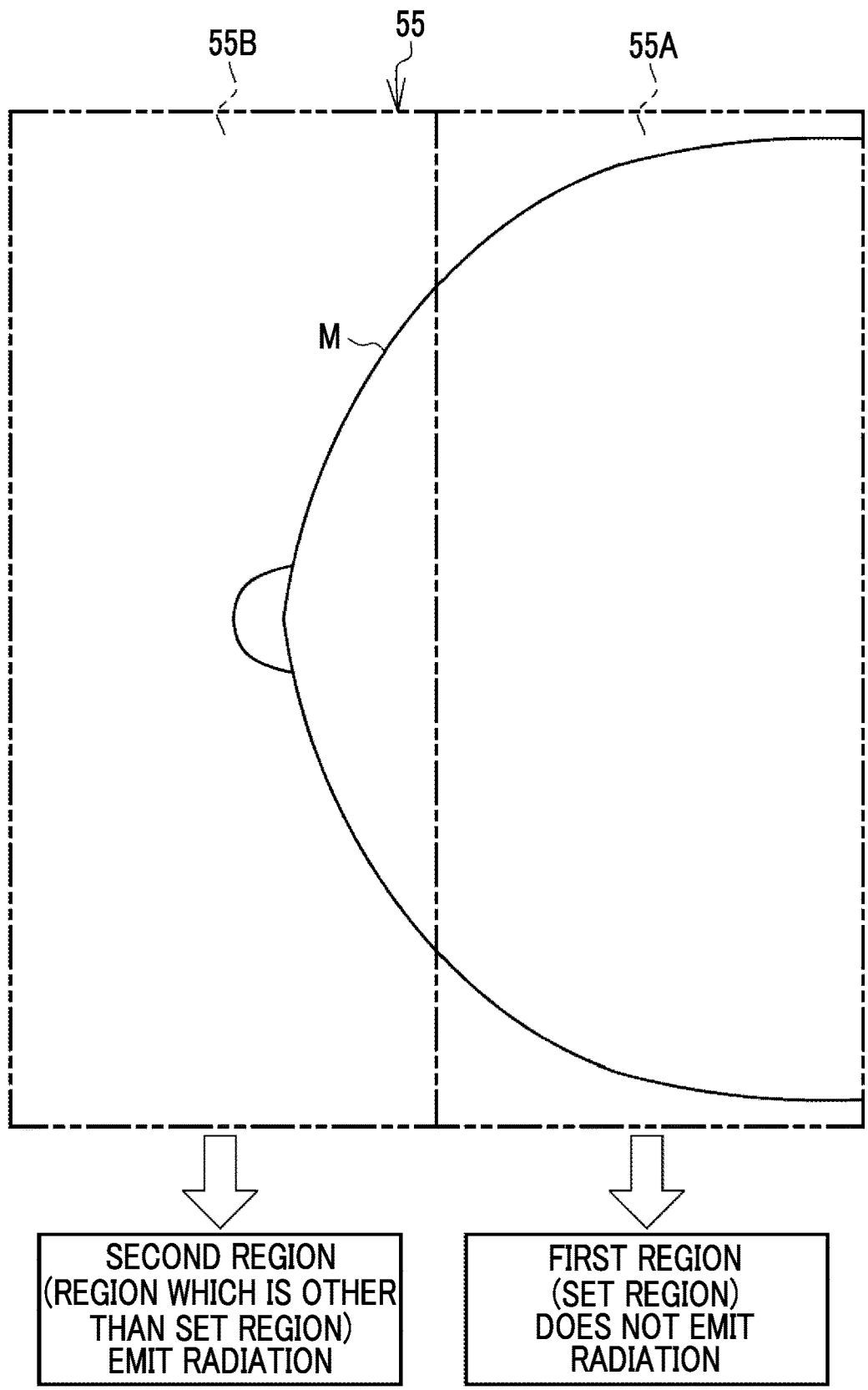
FIG. 14 is a diagram illustrating the scanning position and radiography timing of an ultrasound transceiver according to a second embodiment.

In a second embodiment illustrated in FIG. 14, the radiation source 25 emits the radiation R only in a state in which the ultrasound transceiver 31 is in a region other than a set region. In other words, in a case in which the ultrasound transceiver 31 is in the set region, the radiation source 25 does not emit the radiation R.

Specifically, in a case in which the radiography region 55 is divided into two regions, that is, a first region 55A close to the chest wall CW and a second region 55B away from the chest wall CW as illustrated in FIG. 14, the set region is set to the first region 55A. The radiation source control unit 75 directs the radiation source 25 not to emit the radiation R in a state in which the ultrasound transceiver 31 is in the first region 55A which is the set region. In contrast, the radiation source control unit 75 directs the radiation source 25 to emit the radiation R in a state in which the ultrasound transceiver 31 is in the second region 55B other than the set region.

As illustrated in FIG. 9, in the first embodiment, radiography is performed in a state in which the ultrasound transceiver 31 is disposed at the scanning start position that is closest to the chest wall CW and is in the first region 55A. In the radiographic image RI_1 obtained by the radiography, the image 90 of the ultrasound transceiver 31 is included in the first region 55A and there is no image information of a portion of the breast M which is close to the chest wall CW in the first region 55A.

The portion of the breast M close to the chest wall CW is important as a medical examination target because breast cancer is likely to be metastasized or to recur in the portion of the breast M. For this reason, in the second embodiment, in a case in which the ultrasound transceiver 31 is disposed in the first region 55A, radiography is not performed such that the image information of the portion of the breast M close to the chest wall CW is included in the radiographic image RI_K. Then, the radiographic image RI_K certainly includes the image information of the portion of the breast M close to the chest wall CW and the removed radiographic image RIR generated on the basis of the radiographic image RI_K also include a larger amount of image information of the portion of the breast M which is close to the chest wall CW. Therefore, it is possible to generate the removed radiographic image RIR more suitable for a medical examination.

In the example illustrated in FIG. 9, a state in which the ultrasound transceiver 31 is disposed at the scanning start position and the third position is also the state in which the ultrasound transceiver 31 is disposed at different positions of the radiography region 55. Therefore, if there is no restriction in the second embodiment that the radiation source 25 does not emit the radiation R in a case in which the ultrasound transceiver 31 is in the first region 55A, radiography may be performed in a state in which the ultrasound transceiver 31 is disposed at the scanning start position and the third position.

The set region is not limited to the first region 55A in the above-mentioned example. In a case in which the first region 55A is further divided into two regions, that is, a region close to the chest wall CW and a region away from the chest wall CW, the region close to the chest wall CW (a quarter region close to the chest wall in a case in which the radiography region 55 is divided into four equal regions) may be set as the set region.

Third Embodiment

In a third embodiment illustrated in FIGS. 15A and 15B, the radiation R emitted to the ultrasound transceiver 31 is shielded by the shielding plate 46 of the irradiation field limiter 45. That is, here, the irradiation field limiter 45 is an example of a shielding unit.

FIG. 15A illustrates a case in which the ultrasound transceiver 31 is disposed at the scanning start position. In this case, the radiation source control unit 75 moves the shielding plate 46 of the irradiation field limiter 45 such that the radiation R is not emitted to the ultrasound transceiver 31 at the scanning start position. A non-irradiation-field region 105 is present in a radiographic image RI_1 obtained by shielding the radiation R with the shielding plate 46. Similarly, in FIG. 15B illustrating a case in which the ultrasound transceiver 31 is disposed at the scanning end position, the radiation R is shielded by the shielding plate 46 and the radiation R is not emitted to the ultrasound transceiver 31. The non-irradiation-field region 105 is present in a radiographic image RI_2 obtained in this case. In the third embodiment, the non-irradiation-field region 105 is regarded as the image 90 of the ultrasound transceiver 31 and the generation of the removed radiographic image RIR is performed. In addition, in FIGS. 15A and 15B, for example, the main body portion 24, the movement mechanism 30, and the scanning mechanism 32 are not illustrated.

As such, in the third embodiment, the shielding plate 46 of the irradiation field limiter 45 is moved to shield the radiation R emitted to the ultrasound transceiver 31. Therefore, it is possible to prevent the deterioration of the performance of the ultrasound transceiver 31 caused by the emission of the radiation R.

A shielding unit that shields the emission of the radiation R to the ultrasound transceiver 31 may be provided separately from the irradiation field limiter 45. However, in a case in which the irradiation field limiter 45 is used as the shielding unit as in FIGS. 15A and 15B, it is possible to prevent an increase in cost and size, as compared to the case in which the shielding unit is provided separately from the irradiation field limiter 45.

Fourth Embodiment

Figure 17:
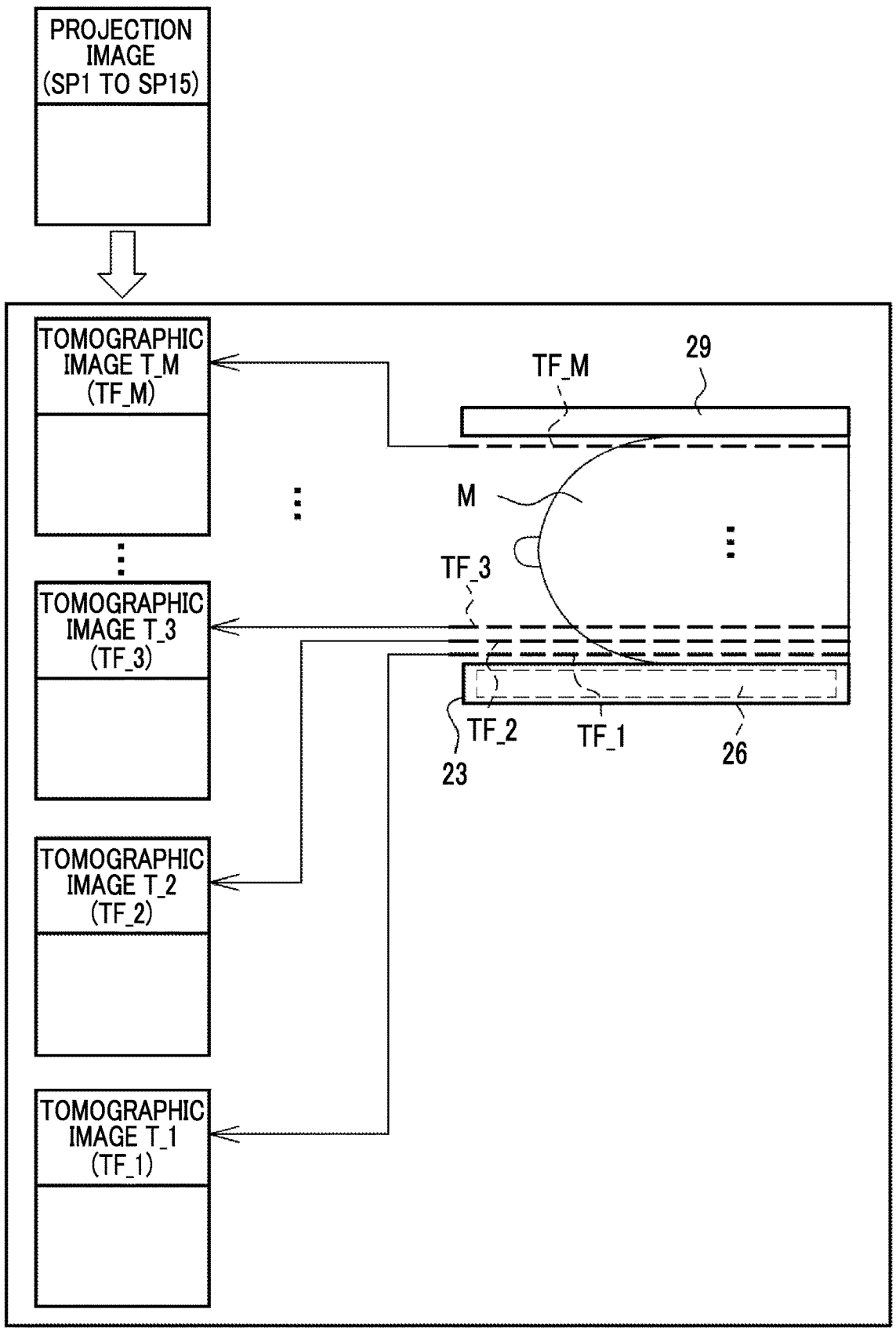
FIG. 17 is a diagram illustrating an aspect in which tomographic images are generated from a plurality of projection images.
Figure 18:
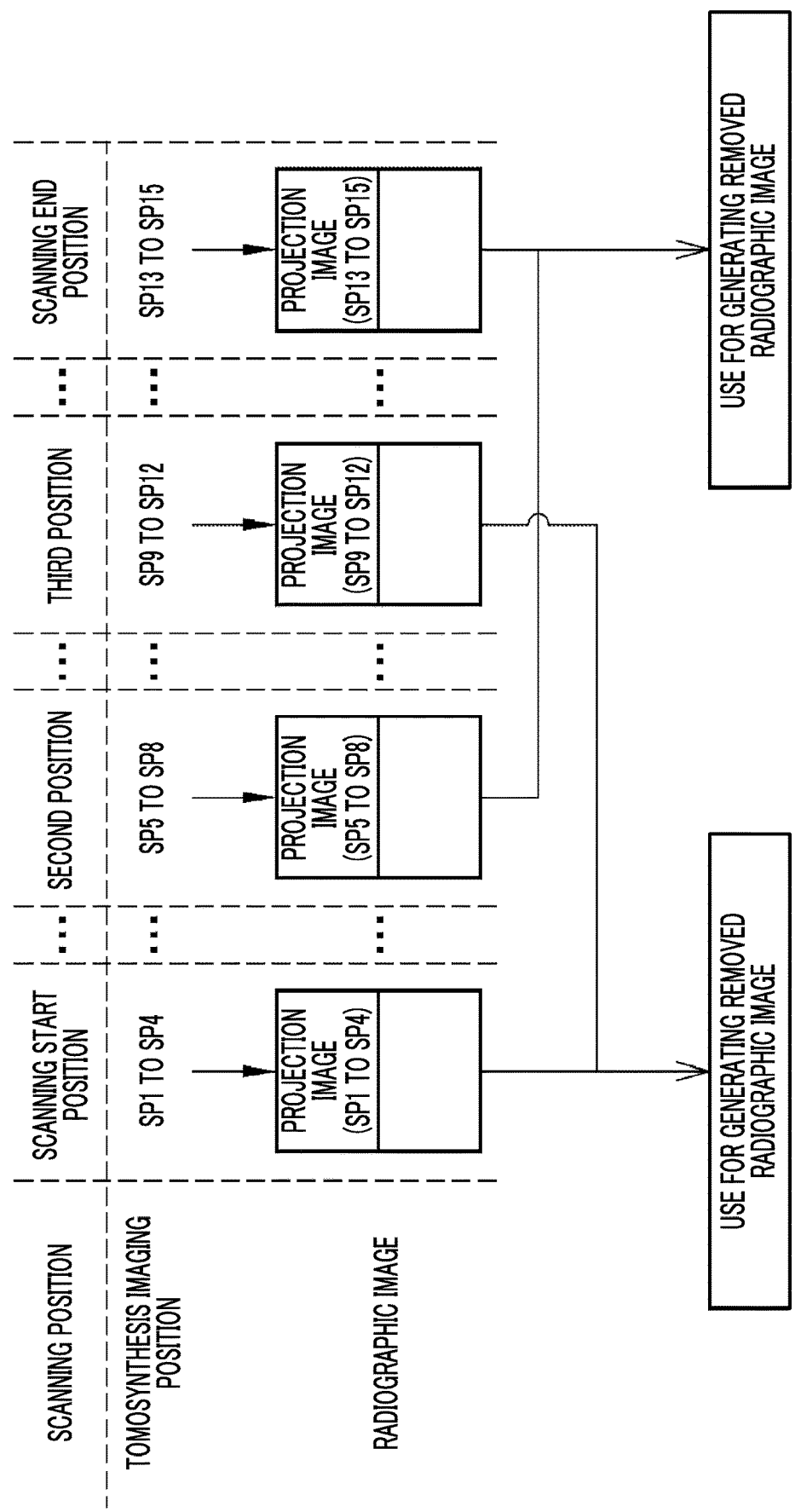
FIG. 18 is a diagram illustrating the scanning position and radiography timing of an ultrasound transceiver according to the fourth embodiment.

In a fourth embodiment illustrated in FIGS. 16 to 18, a mammography apparatus has a tomosynthesis imaging function. A plurality of radiographic images RI_K which are the source of the removed radiographic image RIR are projection images captured by the tomosynthesis imaging function.

In FIG. 16, the mammography apparatus according to the fourth embodiment has a tomosynthesis imaging function that moves the radiation source 25 to a total of 15 positions, that is, positions SP1, SP2, . . . , SP14, and SP15 with respect to the radiation detector 26 and directs the radiation source 25 to emit the radiation R at each of the positions SP1 to SP15. At the positions SP1 to SP15, the radiation R is emitted to the radiography region 55 of the radiation detector 26 at different irradiation angles. The focuses F1 to F15 of the radiation R of the radiation source 25 at the positions SP1 to SP15 are set so as to be linearly arranged at equal intervals D in a lateral direction perpendicular to a height direction and a depth direction. Further, the positions SP1 to SP15 are bilaterally symmetric with respect to a normal line NR that extends from a center point CP of the radiography region 55 such that the position SP8 is disposed on the normal line NR, the positions SP1 to SP7 are disposed on the left side of the normal line NR, and positions SP8 to SP15 are disposed on the right side of the normal line NR. In FIG. 16, the movement trajectory of the radiation source 25 is linear. However, the present disclosure is not limited thereto. The movement trajectory of the radiation source 25 may be an arc shape.

In one tomosynthesis imaging operation, for example, the radiation source 25 is moved in the order of the position SP1, the position SP2, . . . , the position SP14, and the position SP15 and emits the radiation R to the breast M at each of the positions SP1 to SP15. The radiation detector 26 detects the radiation R emitted at each of the positions SP1 to SP15 and outputs a total of 15 projection images at each of the positions SP1 to SP15. In addition, the tomosynthesis imaging function can be applied to each of the CC imaging method and the MLO imaging method.

As illustrated in FIG. 17, the radiographic image generation unit generates tomographic images T_J corresponding to any tomographic planes TF_J (J=1 to M, M is the number of tomographic planes) of the breast M from the plurality of projection images at the plurality of positions SP1 to SP15 obtained by the tomosynthesis imaging illustrated in FIG. 16, using a known method such as a filtered back projection method. The tomographic images T_J are images in which structures in the tomographic planes TF_J have been highlighted.

As illustrated in FIG. 18, the radiation source control unit, the transceiver control unit, the scanning mechanism control unit, and the detector control unit synchronize one tomosynthesis imaging operation with scanning by the ultrasound transceiver 31 illustrated in FIG. 9 from the scanning start position to the scanning end position. Specifically, the positions SP1 to SP4 in the tomosynthesis imaging are matched with the scanning start position of the ultrasound transceiver 31 and the positions SP13 to SP15 in the tomosynthesis imaging are matched with the scanning end position of the ultrasound transceiver 31. In addition, the positions SP5 to SP8 in the tomosynthesis imaging are matched with the second position of the ultrasound transceiver 31 illustrated in FIG. 9 and the positions SP9 to SP12 in the tomosynthesis imaging are matched with the third position illustrated in FIG. 9.

The radiographic image generation unit generates the removed radiographic image RIR on the basis of the plurality of projection images obtained by the tomosynthesis imaging before the tomographic images T_J are generated. Specifically, the radiographic image generation unit generates the removed radiographic image RIR on the basis of the projection images at the positions SP1 to SP4 and the positions SP9 to SP12 and the projection images at the positions SP5 to SP8 and the positions SP13 to SP15. That is, in the fourth embodiment, the plurality of radiographic images RI_K which are the source of the removed radiographic image RIR are the projection images captured by the tomosynthesis imaging function.

However, in the tomosynthesis imaging, since the irradiation angles of the radiation R at the positions SP1 to SP15 are different from each other, it is natural that the states of the breast M and the image 90 of the ultrasound transceiver 31 in a plurality of projection images obtained at the positions SP1 to SP15 are different from each other. Therefore, the radiographic image generation unit performs correction (for example, mirror image inversion, rotation, and distortion correction) for removing the differences between the states of the breast M and the image 90 of the ultrasound transceiver 31 in the plurality of projection images and then generates the removed radiographic image RIR. In addition, as a method for generating the removed radiographic image RIR, the method illustrated in FIG. 10 may be used or the method illustrated in FIG. 13 may be used.

The radiographic image generation unit generates the tomographic image T_J using the removed radiographic image RIR generated on the basis of the plurality of projection images.

As such, in the fourth embodiment, the removed radiographic image RIR is generated on the basis of a plurality of projection images obtained by tomosynthesis imaging. In the related art, performing tomosynthesis imaging in the mammography apparatus has been found to be useful as a method for easily finding lesions such as microcalcifications of the breast M. Therefore, it is possible to obtain image information more useful for a medical examination for the breast M.

Fifth Embodiment

Figure 19:
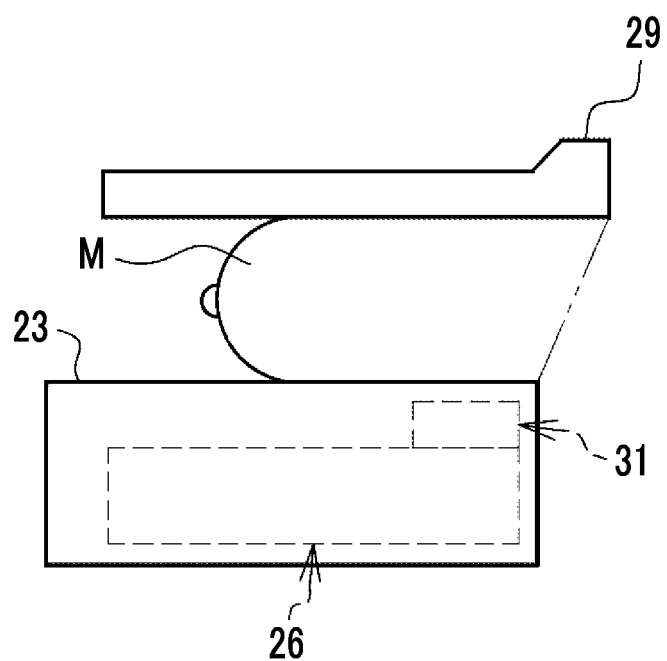
FIG. 19 is a diagram illustrating a fifth embodiment in which an ultrasound transceiver is provided in an imaging table.

In a fifth embodiment illustrated in FIG. 19, the ultrasound transceiver 31 is not provided in the compression plate 29, but is provided in the imaging table 23. In this case, the imaging table 23 is made of a material that transmits the radiation R, the ultrasonic waves US, and the ultrasound echoes UE. This arrangement makes it is possible to capture an ultrasound image of the breast M.

In each of the above-described embodiments, the ultrasound transceiver 31 has the ultrasound transducer array 50 in which the plurality of ultrasound transducers 51 are two-dimensionally arranged. However, the present disclosure is not limited thereto. The ultrasound transceiver 31 may have an ultrasound transducer array in which a plurality of ultrasound transducers are one-dimensionally (linearly) arranged. In each of the above-described embodiments, the ultrasound transceiver 31 performs scanning in the depth direction. However, the ultrasound transceiver 31 may perform scanning in the lateral direction. In addition, scanning in the depth direction and scanning in the lateral direction may be combined such that the ultrasound transceiver performs scanning in an S-shape. Further, ultrasound imaging may be performed while the ultrasound transceiver is continuously moved without being stopped at each scanning position.

For example, in the first embodiment, in two states in which the ultrasound transceiver 31 are at different positions of the radiography region 55, the radiation R is emitted from the radiation source 25 two times and the removed radiographic image RIR is generated on the basis of two radiographic images RI_1 and RI_2 obtained by two irradiation operations. However, the present disclosure is not limited thereto. In two or more states in which the ultrasound transceiver 31 are at different positions of the radiography region 55, the radiation R may be emitted from the radiation source 25 two or more times and the removed radiographic image RIR may be generated on the basis of two or more radiographic images RI_K obtained by two or more irradiation operations. In a case in which the image 90 of the ultrasound transceiver 31 is not disposed at the same position in all of the two or more radiographic images RI_K, radiographic images RI_K in which the positions of the image 90 of the ultrasound transceiver 31 partially overlap each other may be used among the two or more radiographic images RI_K.

There is a radiography timing deviation between the plurality of radiographic images RI_K. For this reason, the movement of the subject H may cause blurring in the plurality of radiographic images RI_K. Therefore, it is preferable to determine whether or not blurring occurs in the plurality of radiographic images RI_K before the removed radiographic image RIR is generated and to correct the blurring in a case in which the blurring occurs. For example, whether or not blurring occurs is determined by extracting a feature point, such as the nipple, in the plurality of radiographic images RI_K, calculating the amount of deviation of the extracted feature point, and comparing the amount of deviation with a threshold value. In a case in which the amount of deviation is equal to or greater than the threshold value, it is determined that blurring has occurred. In addition, as a method for correcting the blurring, for example, a method can be used which moves, with respect to one of the plurality of radiographic images RI_K, other radiographic images RI_K to remove the amount of deviation of the feature point.

Ultrasound imaging may be performed while compressing the breast M with different levels of compression force and elastography may be performed to detect the hardness of the tissues of the breast M on the basis of an ultrasound image obtained the ultrasound imaging.

In each of the above-described embodiments, the computer forming the control device 12 functions as the image processing apparatus. However, the present disclosure is not limited thereto. The operation program 70 may be installed in a computer forming the image DB server 14, the terminal apparatus 15, or another apparatus such that the computer forming the image DB server 14, the terminal apparatus 15, or another apparatus functions as the image processing apparatus. In this case, the acquisition unit does not directly acquire the radiographic image from the radiation detector 26 unlike the second acquisition unit 81 according to, for example, the first embodiment, but reads and acquires the radiographic image which has been output from the radiation detector 26 and then temporarily stored in the storage device.

In each of the above-described embodiments, for example, the following various processors can be used as the hardware structure of processing units performing various processes, such as the radiation source control unit 75, the transceiver control unit 76, the first acquisition unit 77, the scanning mechanism control unit 78, the movement mechanism control unit 79, the detector control unit 80, the second acquisition unit 81, the ultrasound image generation unit 82, the radiographic image generation units 83 and 100, and the display control unit 84. The various processors include a central processing unit (CPU) which is a general-purpose processor executing software (operation program 70) to function as various processing units, a programmable logic device (PLD), such as a field programmable gate array (FPGA), which is a processor whose circuit configuration can be changed after manufacture, and a dedicated electric circuit, such as an application specific integrated circuit (ASIC), which is a processor having a dedicated circuit configuration designed to perform a specific process.

One processing unit may be configured by one of the various processors or a combination of two or more processors of the same type or different types (for example, a combination of a plurality of FPGAs or a combination of a CPU and an FPGA). In addition, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). As such, various processing units are configured by using one or more of the various processors as a hardware structure.

In addition, specifically, an electric circuit (circuitry) obtained by combining circuit elements, such as semiconductor elements, can be used as the hardware structure of the various processors.

It is possible to understand the invention described in the following Supplementary Note 1 from the above description.

Supplementary Note 1

There is provided an image processing apparatus comprising: an acquisition processor that acquires a plurality of radiographic images in which an image of an ultrasound transceiver is disposed at different positions; and a generation processor that generates a removed radiographic image, in which the image of the ultrasound transceiver has been removed, on the basis of the plurality of radiographic images acquired by the acquisition processor.

In the technology according to the present disclosure, the above-mentioned various embodiments and various modification examples may be combined with each other. In addition, the present disclosure is not limited to the above-described embodiments and various configurations can be used without departing from the scope and spirit of the present disclosure.

What is claimed is:

1. A mammography apparatus comprising:
   a radiation source that irradiates a breast with radiation;
   a radiation detector having a radiography region in which pixels that detect the radiation transmitted through the breast are two-dimensionally arranged;
   an ultrasound transceiver that is provided between the radiation source and the radiation detector and has an ultrasound imaging region which is smaller than the radiography region and in which ultrasound transducers that transmit ultrasonic waves to the breast and receive ultrasound echoes from the breast are arranged;
   a scanning mechanism that moves the ultrasound transceiver from a scanning start position to a scanning end position in the radiography region; and
   a processor that directs the radiation source to emit the radiation to the radiation detector and the ultrasound transceiver to generate a plurality of radiographic images and directs the radiation source to emit the radiation in a plurality of states in which the ultrasound transceiver is respectively disposed at a plurality of different positions of the radiography region while the ultrasound transceiver is moved from the scanning start position to the scanning end position such that a region of an image of the ultrasound transceiver is included in each of the plurality of radiographic images.

2. The mammography apparatus according to claim 1, wherein the processor is further configured to:
   generate a removed radiographic image, in which the region corresponding to the image of the ultrasound transceiver has been removed, on the basis of the plurality of radiographic images of the breast in the plurality of states.

3. The mammography apparatus according to claim 2,
wherein the processor generates a plurality of cutout images obtained by cutting out a region other than the region corresponding to the image of the ultrasound transceiver from each of the plurality of radiographic images and combines the plurality of cutout images to generate the removed radiographic image.

4. The mammography apparatus according to claim 1,
wherein the processor directs the radiation source to emit the radiation only in a state in which the ultrasound transceiver is disposed in a region other than a set region.

5. The mammography apparatus according to claim 4,
wherein, in a case in which the radiography region is divided into a first region close to a chest wall and a second region away from the chest wall, the set region is set to the first region.

6. The mammography apparatus according to claim 1, further comprising:
an imaging table in which the radiation detector is accommodated and on which the breast is placed; and
a compression plate that is provided so as to face the imaging table and compresses the breast interposed between the compression plate and the imaging table,
wherein the ultrasound transceiver is provided in the compression plate.

7. The mammography apparatus according to claim 1, further comprising:
an imaging table in which the radiation detector is accommodated and on which the breast is placed,
wherein the ultrasound transceiver is provided in the imaging table.

8. The mammography apparatus according to claim 1, further comprising:
a shielding unit that shields irradiation of the radiation to the ultrasound transceiver.

9. The mammography apparatus according to claim 8,
wherein the shielding unit is an irradiation field limiter that sets an irradiation field of the radiation to the radiography region.

10. The mammography apparatus according to claim 1,
wherein the mammography apparatus has a tomosynthesis imaging function that moves the radiation source to a plurality of positions with respect to the radiation detector and directs the radiation source to emit the radiation at each position, and
the plurality of radiographic images are projection images captured by the tomosynthesis imaging function.

11. The mammography apparatus according to claim 1,
wherein the region of the image of the ultrasound transceiver is included at a different position in each of the plurality of radiographic images.

12. A method for operating a mammography apparatus comprising a radiation source that irradiates a breast with radiation, a radiation detector having a radiography region in which pixels that detect the radiation transmitted through the breast are two-dimensionally arranged, an ultrasound transceiver that is provided between the radiation source and the radiation detector and has an ultrasound imaging region which is smaller than the radiography region and in which ultrasound transducers that transmit ultrasonic waves to the breast and receive ultrasound echoes from the breast are arranged, a scanning mechanism that moves the ultrasound transceiver from a scanning start position to a scanning end position in the radiography region, and a processor, the method comprising:

allowing the processor to direct the radiation source to emit the radiation to the radiation detector and the ultrasound transceiver to generate a plurality of radiographic images and to direct the radiation source to emit the radiation in a plurality of states in which the ultrasound transceiver is respectively disposed at a plurality of different positions of the radiography region while the ultrasound transceiver is moved from the scanning start position to the scanning end position such that a region of an image of the ultrasound transceiver is included in each of the plurality of radiographic images.

13. An image processing apparatus comprising:
a processor, configured to:
direct a radiation source to emit radiation to a radiation detector and an ultrasound transceiver to generate a plurality of radiographic images, wherein the ultrasound transceiver is respectively disposed at a plurality of different positions of a radiography region of the radiation detector, and wherein a region of an image of the ultrasound transceiver is included in each of the plurality of radiographic images; and
generate a removed radiographic image, in which the region corresponding to the image of the ultrasound transceiver has been removed, on the basis of the plurality of radiographic images.

14. The image processing apparatus according to claim 13,
wherein the processor generates a plurality of cutout images obtained by cutting out a region other than the region corresponding to the image of the ultrasound transceiver from each of the plurality of radiographic images, and combines the plurality of cutout images to generate the removed radiographic image.

15. A non-transitory computer-readable storage medium storing a program for operating an image processing apparatus, the program causing a computer to:
direct a radiation source to emit radiation to a radiation detector and an ultrasound transceiver to generate a plurality of radiographic images, wherein the ultrasound transceiver is respectively disposed at a plurality of different positions of a radiography region of the radiation detector, and wherein a region of an image of the ultrasound transceiver is included in each of the plurality of radiographic images; and
generate a removed radiographic image, in which the region corresponding to the image of the ultrasound transceiver has been removed, on the basis of the plurality of radiographic images.

16. A method for operating an image processing apparatus, the method comprising:
directing a radiation source to emit radiation to a radiation detector and an ultrasound transceiver to generate a plurality of radiographic images, wherein the ultrasound transceiver is respectively disposed at a plurality of different positions of a radiography region of the radiation detector, and wherein a region of an image of the ultrasound transceiver is included in each of the plurality of radiographic images; and
generating a removed radiographic image, in which the region corresponding to the image of the ultrasound transceiver has been removed, on the basis of the plurality of radiographic images.

17. A non-transitory computer-readable storage medium storing a program for operating a mammography apparatus comprising a radiation source that irradiates a breast with radiation, a radiation detector having a radiography region in which pixels that detect the radiation transmitted through the breast are two-dimensionally arranged, an ultrasound transceiver that is provided between the radiation source and the radiation detector and has an ultrasound imaging region which is smaller than the radiography region and in which ultrasound transducers that transmit ultrasonic waves to the breast and receive ultrasound echoes from the breast are arranged, and a scanning mechanism that moves the ultrasound transceiver from a scanning start position to a scanning end position in the radiography region, the program causing a computer to execute a process comprising:

directing the radiation to irradiate from the radiation source to the radiation detector and the ultrasound transceiver to generate a plurality of radiographic images and directing the radiation to irradiate from the radiation source in a plurality of states in which the ultrasound transceiver is respectively disposed at a plurality of different positions of the radiography region while the ultrasound transceiver is moved from the scanning start position to the scanning end position such that a region of an image of the ultrasound transceiver is included in each of the plurality of radiographic images.

* * * * *